US010358458B2

(12) United States Patent
Smith et al.

(10) Patent No.: US 10,358,458 B2
(45) Date of Patent: Jul. 23, 2019

(54) 4'-VINYL SUBSTITUTED NUCLEOSIDE DERIVATIVES AS INHIBITORS OF RESPIRATORY SYNCYTIAL VIRUS RNA REPLICATION

(71) Applicant: Riboscience LLC, Palo Alto, CA (US)

(72) Inventors: Mark Smith, San Francisco, CA (US); Klaus G. Klumpp, West Chester, PA (US)

(73) Assignee: RIBOSCIENCE LLC, Palo Alto, CA (US)

( * ) Notice: Subject to any disclaimer, the term of this patent is extended or adjusted under 35 U.S.C. 154(b) by 0 days.

(21) Appl. No.: 14/865,135

(22) Filed: Sep. 25, 2015

(65) Prior Publication Data

US 2016/0264611 A1 Sep. 15, 2016

Related U.S. Application Data

(60) Provisional application No. 62/055,704, filed on Sep. 26, 2014.

(51) Int. Cl.

| | |
|---|---|
| *C07H 19/10* | (2006.01) |
| *C07H 19/20* | (2006.01) |
| *C07H 19/067* | (2006.01) |
| *C07H 19/11* | (2006.01) |
| *C07H 19/167* | (2006.01) |
| *C07H 19/213* | (2006.01) |
| *C07H 19/207* | (2006.01) |
| *A61P 31/14* | (2006.01) |

(52) U.S. Cl.

CPC .............. *C07H 19/10* (2013.01); *A61P 31/14* (2018.01); *C07H 19/067* (2013.01); *C07H 19/11* (2013.01); *C07H 19/167* (2013.01); *C07H 19/20* (2013.01); *C07H 19/207* (2013.01); *C07H 19/213* (2013.01)

(58) Field of Classification Search

None

See application file for complete search history.

(56) References Cited

U.S. PATENT DOCUMENTS

| | | | | |
|---|---|---|---|---|
| 2003/0236216 | A1 | 12/2003 | Devos et al. | |
| 2004/0121980 | A1 | 6/2004 | Martin et al. | |
| 2004/0167096 | A1* | 8/2004 | Cheng et al. | A61K 31/522 514/46 |
| 2007/0042988 | A1 | 2/2007 | Klumpp et al. | |
| 2013/0018011 | A1 | 1/2013 | Javanbakht et al. | |
| 2013/0165400 | A1 | 6/2013 | Beigelman et al. | |
| 2015/0051167 | A1 | 2/2015 | Wang et al. | |
| 2015/0366887 | A1 | 12/2015 | Blatt et al. | |
| 2015/0366888 | A1 | 12/2015 | Blatt et al. | |
| 2016/0052953 | A1* | 2/2016 | Clarke | C07H 19/06 514/49 |

FOREIGN PATENT DOCUMENTS

| | | | | |
|---|---|---|---|---|
| WO | WO-98/16184 | A2 | 4/1998 | |
| WO | WO-98/16184 | A3 | 4/1998 | |
| WO | WO-02/03997 | A1 | 1/2002 | |
| WO | 2003026589 | A2 | 4/2003 | |
| WO | 2003026675 | A1 | 4/2003 | |
| WO | 2005020885 | A2 | 3/2005 | |
| WO | 2007020193 | A2 | 2/2007 | |
| WO | 2007145593 | A1 | 12/2007 | |
| WO | 2009064387 | A2 | 5/2009 | |
| WO | 2009125841 | A1 | 10/2009 | |
| WO | 2010030858 | A1 | 3/2010 | |
| WO | 2011005860 | A2 | 1/2011 | |
| WO | 2011133868 | A2 | 10/2011 | |
| WO | 2013096679 | A1 | 6/2013 | |
| WO | 2013138236 | A1 | 9/2013 | |
| WO | 2013142525 | A1 | 9/2013 | |
| WO | WO14/070771 | * | 5/2014 | C07H 19/06 |
| WO | 2014209979 | A1 | 12/2014 | |
| WO | 2015054465 | A1 | 4/2015 | |
| WO | 2015069939 | A1 | 5/2015 | |
| WO | WO-2015/200219 | A1 | 12/2015 | |
| WO | 2016049415 | A1 | 3/2016 | |

OTHER PUBLICATIONS

Smith et al., Bioorganic and Medicinal Chemistry Letters, 2007, 17(9), pp. 2570-2576.*

Clarke et al., Discovery of β-D-2'-deoxy-2'-α-fluoro-4'-α-cyano-5-aza-7,9-dideaza adenosine as a potent nucleoside inhibitor of respiratory syncytial virus with excellent selectivity over mitochondrial RNA and DNA polymerases, Bioorganic & Medicinal Chemistry Letters, 2015, pp. 2484-2487, vol. 25(12).

Smith et al., Design, synthesis, and antiviral properties of 4'-substituted ribonucleosides as inhibitors of hepatitis C virus replication: The discovery of R1479, Bioorganic & Medicinal Chemistry Letters 17, 2007, pp. 2570-2576, Elsevier.

Girardet et al. Synthesis and Cytotoxicity of 4-Amino-5-oxopyrido [2,3-d] pyrimidine Nucleosides, J. Med. Chem. vol. 43, 2000, pp. 3704-3713.

Kirchhoff et al., Dinucleotides of 4'-C-vinyl- and 5'-C-allylthymidine as substrates for ring-closing metathesis reactions, Tetrahedron Let, Elsevier, vol. 44, No. 34, 2003, pp. 6475-6478.

(Continued)

*Primary Examiner* — Traviss C McIntosh, III

(74) *Attorney, Agent, or Firm* — Mintz, Levin, Cohn, Ferris, Glovsky and Popeo, P.C.

(57) ABSTRACT

The application discloses compounds of Formula I

I wherein the variable substituents are as defined herein. The compounds of Formula I and pharmaceutical compositions comprising compounds of Formula I are useful for the treatment of diseases mediated by RSV.

15 Claims, No Drawings

(56) References Cited

OTHER PUBLICATIONS

Kodama et al., 4'-Ethynyl nucleoside analogs: potent inhibitors of multidrug-resistant human immunodeficiency virus variants in vitro. Antimicrobial Agents and Chemotherapy, American Society for Microbiology, vol. 45, No. 5, 2001, pp. 1539-1546.

Nomura et al., Nucleosides and nucleotides. 185. Synthesis and biological activities of 4'alpha-C-branched-chain sugar pyrimidine nucleosides.Journal of Medicinal Chemistry, American Chemical Society, vol. 42, No. 15, 1999, pp. 2901-2908.

Ohrui et al., A New Paradigm for Developing Antiviral Drugs Exemplified by the Development of Supremely High Anti-HIV Active EFdA, Journal of Antivirals & Antiretrovirals. vol. 6(1), 2014, pp. 032-039.

International Search Report dated Dec. 15, 2015, for PCT Application No. PCT/US2015/052144, filed Sep. 25, 2015, 3 pages.

Wang et al., Study on the Structure-Activity Relationship of New Anti-HIV Nucleoside Derivatives Based on the Support Vector Machine Method, QSAR & Combinatorial Science. vol. 26, 2007, No. 2, 161-172.

Written Opinion dated Dec. 15, 2015, for PCT Application No. PCT/US2015/052144, filed Sep. 25, 2015, 4 pages.

\* cited by examiner

4'-VINYL SUBSTITUTED NUCLEOSIDE DERIVATIVES AS INHIBITORS OF RESPIRATORY SYNCYTIAL VIRUS RNA REPLICATION

CROSS-REFERENCE TO RELATED APPLICATIONS

This application claims priority to U.S. provisional application Ser. No. 62/055,704, filed Sep. 26, 2014, the disclosure of which is incorporated herein by reference and is commonly owned.

FIELD OF THE INVENTION

The application relates to nucleoside derivatives as inhibitors of Respiratory Syncytial Virus (RSV) RNA replication. In particular, the instant disclosure is concerned with the use of purine and pyrimidine nucleoside derivatives as inhibitors of RSV RNA replication and pharmaceutical compositions containing such compounds.

RSV virus is the leading cause of seasonal respiratory disease throughout the world. Patients infected with RSV are at risk of developing severe respiratory disease, which can result in long-lasting complications or death (Lee, N. et al. Clin Infect Dis. 2013 57(8):1069-77; Nair, H. et al. Lancet. 2010 375(9725) 1545-55).

Many of the drugs approved for the treatment of viral infections are nucleosides or nucleoside analogues and most of these nucleoside analogue drugs inhibit viral replication, following conversion to the corresponding triphosphates, through inhibition of the viral polymerase enzymes. The nucleoside triphosphate analogs are therefore the active inhibitors of the target enzyme. The delivery of nucleoside analogs to virus infected target cells therefore requires a precursor that can enter the target cells. This may be a nucleoside analog, if the target cells have the capacity to convert the nucleoside analog to a nucleoside triphosphate derivative, or a nucleoside phosphate analog that can be converted to the active triphosphate in the target cell (Klumpp, K. et al. Hepatitis C: Antiviral Drug Discovery and Development, Nucleoside Inhibitors of Hepatitis C Virus, Caister Academic Press, Norwich, UK, 2011, pp. 293-311).

RSV is a negative strand RNA virus and belongs to the family of Paramyxoviridae. The viral genome encodes a RNA-dependent RNA polymerase (L protein) that is essential for transcription and replication of RSV. The RSV polymerase is incorporated into RSV virions and carried together with the viral negative strand RNA into newly infected cells. Inhibitors of the RSV L-protein have been shown to possess antiviral activity, consistent with the essential nature of the L-protein function for RSV replication (Tiong-Yip, C. L. et al. Antimicrob. Agents Chemother. 2014 58(7) 3867-3873; Xiong, H. et al. Bioorg. Med. Chem. Lett. 2013 23(24) 6789-6793; Mason, S. W. Nucleic Acids Res. 2004 32(16) 4758-4767).

Because RSV virus continues to be the leading cause of seasonal respiratory disease throughout the world, causes risk of developing severe respiratory disease, which can result in long-lasting complications or death, there exists a need in the field for improved forms of treatment of RSV mediated diseases.

SUMMARY OF THE INVENTION

The compounds of Formula I and pharmaceutical compositions comprising said compounds are useful for the treatment of diseases mediated by RSV.

The application provides a compound of Formula I

I 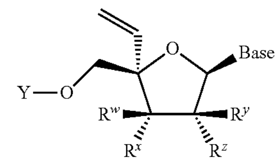 wherein:

Y is H or P(=X)(R)(R');

R is O—$R^1$ or NHC($R^{2a}$)($R^{2b}$)C(=O)O$R^3$;

R' is N($R^4$)C($R^{2a}$)($R^{2b}$)C(=O)O$R^3$, —OP(=O)(OH)OP(=O)(OH)OH, or —O$R^3$;

$R^1$ is H, lower alkyl, lower haloalkyl, or aryl, wherein aryl is phenyl or naphthyl, optionally substituted with one or more lower alkyl, lower alkenyl, lower alkynyl, lower alkoxy, halo, lower haloalkyl, —N($R^{1a}$)$_2$, acylamino, —$SO_2$N($R^{1a}$)$_2$, —C(=O)$R^{1b}$, —$SO_2R^{1c}$, —NH$SO_2R^{1c}$, nitro, cyano, or $R^{1''}$;

each $R^{1a}$ is independently H or lower alkyl;

each $R^{1b}$ is independently —O$R^{1a}$ or —N($R^{1a}$)$_2$;

each $R^{1c}$ is lower alkyl;

each $R^{2a}$ and $R^{2b}$ is independently H, lower alkyl, —$(CH_2)_r$N($R^{1a}$)$_2$, lower hydroxyalkyl, —$CH_2$SH, —($CH_2$)S$(O)_p$Me, —$(CH_2)_n$NHC(=NH)$NH_2$, (1H-indol-3-yl)Me, (1H-indol-4-yl)Me, —$(CH_2)_m$C(=O)$R^{1b}$, aryl or aryl lower alkyl, wherein aryl and aryl lower alkyl are optionally substituted with one or more hydroxy, lower alkyl, lower alkoxy, halo, nitro or cyano;

m is 0, 1, or 2;

n is 1, 2, or 3;

p is 1 or 2;

r is 1 or 2;

or $R^{2a}$ is H and $R^{2b}$ and $R^4$ together form $(CH_2)_n$;

each $R^3$ is independently H, lower alkyl, lower haloalkyl, phenyl or phenyl lower alkyl, wherein phenyl and phenyl lower alkyl are optionally substituted with lower alkoxy;

or $R^3$ and $R^{1''}$ together form $CH_2$;

each $R^4$ is independently H, lower alkyl;

or $R^{2b}$ and $R^4$ together form $(CH_2)_3$;

each of $R^w$, $R^x$, and $R^y$ is independently H, OH, or F;

$R^z$ is H or OH;

or $R^3$ and $R^x$ together form a bond;

or $R^1$ and $R^x$ together form a bond;

X is O or S; and

Base is uracil, cytosine, guanine, adenine, thymine, or heterocycloalkyl, each of which may optionally be substituted with one or more hydroxy, lower alkyl, lower alkoxy, halo, nitro or cyano;

or a pharmacologically acceptable salt thereof.

The application provides the compounds of Formula I which are useful for the prevention or treatment of diseases mediated by RSV, pharmaceutical compositions comprising compounds of Formula I, compounds that result in the formation of compounds of Formula I in vivo during said treatment, or pharmaceutical compositions comprising compounds that result in the formation of compounds of Formula I in vivo during said treatment.

The application provides a method for preventing or treating RSV infection comprising administering to a patient in need thereof a therapeutically effective amount of a compound of Formula I or a compound resulting in the formation of a compound of Formula I in vivo.

The application provides a composition comprising a compound of Formula I, or a compound resulting in the formation of a compound of Formula I in vivo, and a pharmaceutically acceptable excipient.

DETAILED DESCRIPTION OF THE INVENTION

The compounds of Formula I are efficacious as antiviral drugs for the treatment of RSV infections in human. Administration of the compounds of Formula I inhibits RSV replication in infected cells by the formation of the nucleoside 5'-triphosphate derivatives of the compounds of Formula I, as inhibitors of RSV polymerase.

Definitions

The term "alkyl" as used herein denotes a straight or branched chain hydrocarbon residue containing 1 to 12 carbon atoms. Preferably, the term "alkyl" denotes a straight or branched chain hydrocarbon residue containing 1 to 7 carbon atoms. Most preferred are methyl, ethyl, propyl, isopropyl, n-butyl, isobutyl, tert-butyl or pentyl. The alkyl may be unsubstituted or substituted. The substituents are selected from one or more of cycloalkyl, nitro, amino, alkyl amino, dialkyl amino, alkyl carbonyl and cycloalkyl carbonyl.

The term "cycloalkyl" as used herein denotes an optionally substituted cycloalkyl group containing 3 to 7 carbon atoms, e.g. cyclopropyl, cyclobutyl, cyclopentyl, cyclohexyl or cycloheptyl.

The term "alkoxy" as used herein denotes an optionally substituted straight or branched chain alkyl-oxy group wherein the "alkyl" portion is as defined above such as methoxy, ethoxy, n-propyloxy, i-propyloxy, n-butyloxy, i-butyloxy, tert-butyloxy, pentyloxy, hexyloxy, heptyloxy including their isomers.

The term "alkoxyalkyl" as used herein denotes an alkoxy group as defined above which is bonded to an alkyl group as defined above. Examples are methoxymethyl, methoxyethyl, methoxypropyl, ethoxymethyl, ethoxyethyl, ethoxypropyl, propyloxypropyl, methoxybutyl, ethoxybutyl, propyloxybutyl, butyloxybutyl, tert-butyloxybutyl, methoxypentyl, ethoxypentyl, propyloxypentyl including their isomers.

The term "alkenyl" as used herein denotes an unsubstituted or substituted hydrocarbon chain radical having from 2 to 7 carbon atoms, preferably from 2 to 4 carbon atoms, and having one or two olefinic double bonds, preferably one olefinic double bond. Examples are vinyl, 1-propenyl, 2-propenyl (allyl) or 2-butenyl (crotyl).

The term "alkynyl" as used herein denotes an unsubstituted or substituted hydrocarbon chain radical having from 2 to 7 carbon atoms, preferably 2 to 4 carbon atoms, and having one or where possible two triple bonds, preferably one triple bond. Examples are ethynyl, 1-propynyl, 2-propynyl, 1-butynyl, 2-butynyl or 3-butynyl.

The term "hydroxyalkyl" as used herein denotes a straight or branched chain alkyl group as defined above wherein 1, 2, 3 or more hydrogen atoms are substituted by a hydroxy group. Examples are hydroxymethyl, 1-hydroxyethyl, 2-hydroxyethyl, 1-hydroxypropyl, 2-hydroxypropyl, 3-hydroxypropyl, hydroxyisopropyl, hydroxybutyl and the like.

The term "haloalkyl" as used herein denotes a straight or branched chain alkyl group as defined above wherein 1, 2, 3 or more hydrogen atoms are substituted by a halogen. Examples are 1-fluoromethyl, 1-chloromethyl, 1-bromomethyl, 1-iodomethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-dichloroethyl, 3-bromopropyl or 2,2,2-trifluoroethyl and the like.

The term "alkylthio" as used herein denotes a straight or branched chain (alkyl)S— group wherein the "alkyl" portion is as defined above. Examples are methylthio, ethylthio, n-propylthio, i-propylthio, n-butylthio, i-butylthio or tert-butylthio.

The term "aryl" as used herein denotes an optionally substituted phenyl or naphthyl group (e.g. 1-naphthyl, 2-naphthyl or 3-naphthyl). Suitable substituents for aryl can be selected from those named for alkyl, in addition however, halogen, hydroxy and optionally substituted alkyl, haloalkyl, alkenyl, alkynyl and aryloxy are substituents which can be added to the selection.

The term "heterocycloalkyl" or "heterocyclyl" as used herein denotes optionally substituted saturated, partially unsaturated or aromatic monocyclic, bicyclic or tricyclic heterocyclic systems which contain one or more hetero atoms selected from nitrogen, oxygen and sulfur which can also be fused to an optionally substituted saturated, partially unsaturated or aromatic monocyclic carbocycle or heterocycle.

Examples of suitable heterocycles are oxazolyl, isoxazolyl, furyl, tetrahydrofuryl, 1,3-dioxolanyl, dihydropyranyl, 2-thienyl, 3-thienyl, pyrazinyl, isothiazolyl, dihydrooxazolyl, pyrimidinyl, tetrazolyl, 1-pyrrolidinyl, 2-pyrrolidinyl, 3-pyrrolidinyl, pyrrolidinonyl, (N-oxide)-pyridinyl, 1-pyrrolyl, 2-pyrrolyl, triazolyl e.g. 1,2,3-triazolyl or 1,2,4-triazolyl, 1-pyrazolyl, 2-pyrazolyl, 4-pyrazolyl, piperidinyl, morpholinyl (e.g. 4-morpholinyl), thiomorpholinyl (e.g. 4-thiomorpholinyl), thiazolyl, pyridinyl, dihydrothiazolyl, imidazolidinyl, pyrazolinyl, piperazinyl, 1-imidazolyl, 2-imidazolyl, 4-imidazolyl, thiadiazolyl e.g. 1,2,3-thiadiazolyl, 4-methylpiperazinyl, 4-hydroxypiperidin-1-yl.

Suitable substituents for heterocycloalkyl can be selected from those named for alkyl, in addition however, optionally substituted alkyl, alkenyl, alkynyl, an oxo group (═O) or aminosulphonyl are substituents which can be added to the selection.

The term "acyl" ("alkylcarbonyl") as used herein denotes a group of formula C(═O)R wherein R is hydrogen, an unsubstituted or substituted straight or branched chain hydrocarbon residue containing 1 to 7 carbon atoms or a phenyl group. Most preferred acyl groups are those wherein R is hydrogen, an unsubstituted straight chain or branched hydrocarbon residue containing 1 to 4 carbon atoms or a phenyl group.

The term halogen stands for fluorine, chlorine, bromine or iodine, and preferably fluorine, chlorine, or bromine.

In the pictorial representation of the compounds given throughout this application, a thickened tapered line (◂▬▬) indicates a substituent which is above the plane of the ring to which the asymmetric carbon belongs and a dotted line (••׀׀׀׀׀) indicates a substituent which is below the plane of the ring to which the asymmetric carbon belongs.

Compounds of Formula I exhibit stereoisomerism. These compounds can be any isomer of the compound of Formula I or mixtures of these isomers. The compounds and intermediates of the present invention having one or more asymmetric carbon atoms may be obtained as racemic mixtures of stereoisomers which can be resolved.

Compounds of Formula I may exhibit tautomerism, which means that the compounds of Formula I can exist as two or more chemical compounds that are capable of facile interconversion. In many cases it merely means the exchange of a hydrogen atom between two other atoms, to either of which it forms a covalent bond. Tautomeric compounds exist in a mobile equilibrium with each other, so that attempts to prepare the separate substances usually result in the formation of a mixture that shows all the chemical and physical properties to be expected on the basis of the structures of the components.

The most common type of tautomerism is that involving carbonyl, or keto, compounds and unsaturated hydroxyl compounds, or enols. The structural change is the shift of a hydrogen atom between atoms of carbon and oxygen, with the rearrangement of bonds. For example, in many aliphatic aldehydes and ketones, such as acetaldehyde, the keto form is the predominant one; in phenols, the enol form is the major component.

Compounds of Formula I which are basic can form pharmaceutically acceptable salts with inorganic acids such as hydrohalic acids (e.g. hydrochloric acid and hydrobromic acid), sulfuric acid, nitric acid and phosphoric acid, and the like, and with organic acids (e.g. with acetic acid, tartaric acid, succinic acid, fumaric acid, maleic acid, malic acid, salicylic acid, citric acid, methanesulfonic acid and p-toluene sulfonic acid, and the like). The formation and isolation of such salts can be carried out according to methods known in the art.

Inhibitors of RSV

The application provides a compound of Formula I

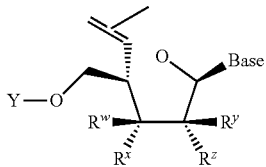

wherein:
Y is H or $P(=X)(R)(R')$;
  R is $O-R^1$ or $NHC(R^{2a})(R^{2b})C(=O)OR^3$;
  R' is $N(R^4)C(R^{2a})(R^{2b})C(=O)OR^3$, $-OP(=O)(OH)OP(=O)(OH)OH$, or $-OR^3$;
  $R^1$ is H, lower alkyl, lower haloalkyl, or aryl, wherein aryl is phenyl or naphthyl, optionally substituted with one or more lower alkyl, lower alkenyl, lower alkynyl, lower alkoxy, halo, lower haloalkyl, $-N(R^{1a})_2$, acylamino, $-SO_2N(R^{1a})_2$, $-C(=O)R^{1b}$, $-SO_2R^{1c}$, $-NHSO_2R^{1c}$, nitro, cyano, or $R^{1''}$;
  each $R^{1a}$ is independently H or lower alkyl;
  each $R^{1b}$ is independently $-OR^{1a}$ or $-N(R^{1a})_2$;
  each $R^{1c}$ is lower alkyl;
  each $R^{2a}$ and $R^{2b}$ is independently H, lower alkyl, $-(CH_2)_nN(R^{1a})_2$, lower hydroxyalkyl, $-CH_2SH$, $-(CH_2)S(O)_pMe$, $-(CH_2)_nNHC(=NH)NH_2$, (1H-indol-3-yl)Me, (1H-indol-4-yl)Me, $-(CH_2)_mC(=O)R^{1b}$, aryl or aryl lower alkyl, wherein aryl and aryl lower alkyl are optionally substituted with one or more hydroxy, lower alkyl, lower alkoxy, halo, nitro or cyano;
    m is 0, 1, or 2;
    n is 1, 2, or 3;
    p is 1 or 2;
    r is 1 or 2;
  or $R^{2a}$ is H and $R^{2b}$ and $R^4$ together form $(CH_2)_n$;
  each $R^3$ is independently H, lower alkyl, lower haloalkyl, phenyl or phenyl lower alkyl, wherein phenyl and phenyl lower alkyl are optionally substituted with lower alkoxy;
  or $R^3$ and $R^{1''}$ together form $CH_2$;
  each $R^4$ is independently H, lower alkyl;
  or $R^{2b}$ and $R^4$ together form $(CH_2)_3$;
each of $R^w$, $R^x$, $R^y$ and $R^z$ is independently H, OH, or F;
or $R^3$ and $R^x$ together form a bond;
or $R^1$ and $R^x$ together form a bond;
X is O or S;
Base is uracil, cytosine, guanine, adenine, thymine, or heterocycloalkyl, each of which may optionally be substituted with one or more hydroxy, lower alkyl, lower alkoxy, halo, nitro or cyano;
with the proviso that when $R^y$ is H or F and $R^x$ is OH, $R^z$ is not F; and
with the proviso that when $R^x$ and $R^z$ are both H, and $R^w$ is OH, $R^y$ is not F;
or a pharmacologically acceptable salt thereof.

The application provides a compound of Formula I

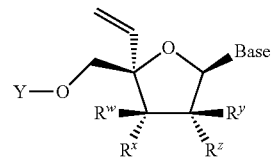

wherein:
Y is H or $P(=X)(R)(R')$;
  R is $O-R^1$ or $NHC(R^{2a})(R^{2b})C(=O)OR^3$;
  R' is $N(R^4)C(R^{2a})(R^{2b})C(=O)OR^3$, $-OP(=O)(OH)OP(=O)(OH)OH$, or $-OR^3$;
  $R^1$ is H, lower alkyl, lower haloalkyl, or aryl, wherein aryl is phenyl or naphthyl, optionally substituted with one or more lower alkyl, lower alkenyl, lower alkynyl, lower alkoxy, halo, lower haloalkyl, $-N(R^{1a})_2$, acylamino, $-SO_2N(R^{1a})_2$, $-C(=O)R^{1b}$, $-SO_2R^{1c}$, $-NHSO_2R^{1c}$, nitro, cyano, or $R^{1''}$;
  each $R^{1a}$ is independently H or lower alkyl;
  each $R^{1b}$ is independently $-OR^{1a}$ or $-N(R^{1a})_2$;
  each $R^{1c}$ is lower alkyl;
  each $R^{2a}$ and $R^{2b}$ is independently H, lower alkyl, $-(CH_2)_nN(R^{1a})_2$, lower hydroxyalkyl, $-CH_2SH$, $-(CH_2)S(O)_pMe$, $-(CH_2)_nNHC(=NH)NH_2$, (1H-indol-3-yl)Me, (1H-indol-4-yl)Me, $-(CH_2)_mC(=O)R^{1b}$, aryl or aryl lower alkyl, wherein aryl and aryl lower alkyl are optionally substituted with one or more hydroxy, lower alkyl, lower alkoxy, halo, nitro or cyano;
    m is 0, 1, or 2;
    n is 1, 2, or 3;
    p is 1 or 2;
    r is 1 or 2;
  or $R^{2a}$ is H and $R^{2b}$ and $R^4$ together form $(CH_2)_n$;
  each $R^3$ is independently H, lower alkyl, lower haloalkyl, phenyl or phenyl lower alkyl, wherein phenyl and phenyl lower alkyl are optionally substituted with lower alkoxy;
  or $R^3$ and $R^{1''}$ together form $CH_2$;
  each $R^4$ is independently H, lower alkyl;
  or $R^{2b}$ and $R^4$ together form $(CH_2)_3$;
each of $R^w$, $R^x$, and $R^y$ is independently H, OH, or F;
$R^z$ is H or OH;
or $R^3$ and $R^x$ together form a bond;
or $R^1$ and $R^x$ together form a bond;
X is O or S; and Base is uracil, cytosine, guanine, adenine, thymine, or heterocycloalkyl, each of which may optionally be substituted with one or more hydroxy, lower alkyl, lower alkoxy, halo, nitro or cyano;

or a pharmacologically acceptable salt thereof.

The application provides the above compound of Formula I, wherein $R^z$ is H.

The application provides either of the above compounds of Formula I, wherein $R^y$ is OH.

The application provides any one of the above compounds of Formula I, wherein $R^w$ is H.

The application provides any one of the above compounds of Formula I, wherein $R^x$ is OH.

The application alternatively provides any one of the above compounds of Formula I, wherein R' is O—$R^3$, $R^3$ is lower alkyl, R is —$OR^1$, and $R^1$ and $R^x$ together form a bond.

The application alternatively provides any one of the above compounds of Formula I, wherein R is —$OR^1$, $R^1$ is phenyl substituted with $R^{1''}$, R' is —$OR^3$, and $R^3$ and $R^{1''}$ together form $CH_2$.

The application provides any one of the above compounds of Formula I, wherein X is O.

The application alternatively provides any one of the above compounds of Formula I, wherein X is S.

The application provides any one of the above compounds of Formula I, wherein R is O—$R^1$, and $R^1$ is phenyl optionally substituted with methoxy.

The application alternatively provides any one of the above compounds of Formula I, wherein R is O—$R^1$, and $R^1$ is naphthyl.

The application provides any one of the above compounds of Formula I, wherein R' is $N(R^4)C(R^{2a})(R^{2b})C(=O)OR^3$, $R^4$ is H, $R^{2a}$ is H, $R^{2b}$ is methyl, and $R^3$ is isopropyl.

The application alternatively provides any one of the above compounds of Formula I, wherein R' is —OP(=O)(OH)OP(=O)(OH)OH.

The application provides any one of the above compounds of Formula I, wherein Base is cytidine optionally substituted with halo.

The application alternatively provides any one of the above compounds of Formula I, wherein Base is uridine optionally substituted with halo.

The application alternatively provides any one of the above compounds of Formula I, wherein Base is guanosine.

The application alternatively provides any one of the above compounds of Formula I, wherein Base is adenosine.

The application provides a compound of Formula I selected from the group consisting of:

4'-Vinyluridine-5'-(O-phenyl-N—(S)-1-(isopropoxycarbonyl)ethyl phosphoramidate;
4'-Vinyluridine-5'-(O-1-naphthyl-N—(S)-1-(isopropoxycarbonyl)ethyl phosphoramidate;
4'-Vinyluridine-5'-(O-1-naphthyl-N—(S)-1-(i2,2-dimethylpropoxycarbonyl)ethyl phosphoramidate;
4'-Vinyluridine-5'-(O-1-naphthyl-N—(S)-1-(3,3-dimethylbutoxycarbonyl)ethyl phosphoramidate;
4'-Vinyluridine-5'-(O-1-naphthyl-N—(S)-1-(benzyloxycarbonyl)ethyl phosphoramidate;
4'-Vinyluridine-5'-(O-1-naphthyl-N—(S)-1-(hexoxycarbonyl)ethyl phosphoramidate;
4'-Vinyluridine-5'-(O-1-naphthyl-N—(S)-1-(cyclopentoxycarbonyl)ethyl phosphoramidate;
4'-Vinyluridine-5'-(O-1-naphthyl-N—(S)-1-(cyclohexoxycarbonyl)ethyl phosphoramidate;
4'-Vinyluridine-5'-(O-2-naphthyl-N—(S)-1-(isopropoxycarbonyl)ethyl phosphoramidate;
4'-Vinyluridine-5'-{N,N'-bis[(S)-1-(isopropoxycarbonyl)ethyl]phosphorodiamidate};
4'-Vinyluridine-5'-{N,N'-bis[(S)-1-(2,2-dimethylpropoxycarbonyl)ethyl]phosphorodiamidate};
4'-Vinyluridine-5'-{N,N'-bis[(S)-1-(3,3-dimethylbutoxycarbonyl)ethyl]phosphorodiamidate};
4'-Vinyluridine-5'-{N,N'-bis[(S)-1-(benzyloxycarbonyl)ethyl]phosphorodiamidate};
4'-Vinyluridine-5'-{N,N'-bis[(S)-1-(hexoxycarbonyl)ethyl]phosphorodiamidate};
4'-Vinyluridine-5'-{N,N'-bis[(S)-1-(cyclopentoxycarbonyl)ethyl]phosphorodiamidate};
4'-Vinyluridine-5'-{N,N'-bis[(S)-1-(cyclohexoxycarbonyl)ethyl]phosphorodiamidate};
4'-Vinyl-5'-O-(2-oxido-4-H-1,3,2-benzodioxaphosphorin-2-yl)-uridine;
4'-Vinyl-5'-O-[bis(4-methoxyphenoxy)phosphinyl] uridine;
4'-Vinyluridine-3',5'-cyclic phosphoric acid isopropyl ester;
4'-Vinylcytidine-5'-(O-phenyl-N—(S)-1-(ethoxycarbonyl)ethyl phosphoramidate;
4'-Vinylcytidine-5'-(O-phenyl-N—(S)-1-(isopropoxycarbonyl)ethyl phosphoramidate;
4'-Vinylcytidine-5'-(O-phenyl-N—(S)-1-(neopentoxycarbonyl)ethyl phosphoramidate;
4'-Vinylcytidine-5'-(O-phenyl-N—(S)-1-(benzyloxycarbonyl)ethyl phosphoramidate;
4'-Vinylcytidine-5'-(O-1-naphthyl-N—(S)-1-(isopropoxycarbonyl)ethyl phosphoramidate;
4'-Vinylcytidine-5'-(O-1-naphthyl-N—(S)-1-(2,2-dimethylpropoxycarbonyl)ethyl phosphoramidate;
4'-Vinylcytidine-5'-(O-1-naphthyl-N—(S)-1-(benzyloxycarbonyl)ethyl phosphoramidate;
4'-Vinylcytidine-5'-(O-1-naphthyl-N—(S)-1-(3,3-dimethybutoxycarbonyl)ethyl phosphoramidate;
4'-Vinylcytidine-5'-(O-1-naphthyl-N—(S)-1-(pentoxycarbonyl)ethyl phosphoramidate;
4'-Vinylcytidine-5'-(O-1-naphthyl-N—(S)-1-(hexoxycarbonyl)ethyl phosphoramidate;
4'-Vinylcytidine-5'-(O-1-naphthyl-N—(S)-1-(cyclohexoxycarbonyl)ethyl phosphoramidate;
4'-Vinylcytidine-5'-(O-2-naphthyl-N—(S)-1-(isopropoxycarbonyl)ethyl phosphoramidate;
4'-Vinylcytidine-5'-{N,N'-bis[(S)-1-(isopropoxycarbonyl)ethyl]phosphorodiamidate};
4'-Vinylcytidine-5'-{N,N'-bis[(S)-1-(2,2-dimethylpropoxycarbonyl)ethyl]phosphorodiamidate};
4'-Vinylcytidine-5'-{N,N'-bis[(S)-1-benzyloxycarbonyl)ethyl]phosphorodiamidate};
4'-Vinylcytidine-5'-{N,N'-bis[(S)-1-(3,3-dimethylbutoxycarbonyl)ethyl]phosphorodiamidate};
4'-Vinylcytidine-5'-{N,N'-bis[(S)-1-(hexoxycarbonyl)ethyl]phosphorodiamidate};
4'-Vinylcytidine-5'-{N,N'-bis[(S)-1-(cyclohexoxycarbonyl)ethyl]phosphorodiamidate};
4'-Vinyl-5'-O-(2-oxido-4-H-1,3,2-benzodioxaphosphorin-2-yl)-cytidine;
4'-Vinyl-5'-O-[bis(4-methoxyphenoxy)phosphinyl]cytidine;
4'-Vinylcytidine-3',5'-cyclic phosphoric acid isopropyl ester;
4'-Vinyladenosine-5'-(O-phenyl-N—(S)-1-(isopropoxycarbonyl)ethyl phosphoramidate;
4'-Vinyladenosine-5'-(O-1-naphthyl-N—(S)-1-(isopropoxycarbonyl)ethyl phosphoramidate;
4'-Vinyladenosine-5'-(O-2-naphthyl-N—(S)-1-(isopropoxycarbonyl)ethyl phosphoramidate;
4'-Vinyladenosine-5'-{N,N'-bis[(S)-1-(isopropoxycarbonyl)ethyl]phosphorodiamidate;

4'-Vinyl-5'-O-(2-oxido-4-H-1,3,2-benzodioxaphosphorin-2-yl)-adenosine;
4'-Vinyl-5'-O-[bis(4-methoxyphenoxy)phosphinyl]adenosine;
4'-Vinyladenosine-3',5'-cyclic phosphoric acid isopropyl ester;
4'-Vinylguanosine-5'-(O-phenyl-N—(S)-1-(isopropoxycarbonyl)ethyl phosphoramidate;
4'-Vinylguanosine-5'-(O-1-naphthyl-N—(S)-1-(isopropoxycarbonyl)ethyl phosphoramidate;
4'-Vinylguanosine-5'-(O-2-naphthyl-N—(S)-1-(isopropoxycarbonyl)ethyl phosphoramidate;
4'-Vinylguanosine-5'-{N,N'-bis[(S)-1-(isopropoxycarbonyl)ethyl]phosphorodiamidate;
4'-Vinyl-5'-O-(2-oxido-4-H-1,3,2-benzodioxaphosphorin-2-yl)-guanosine;
4'-Vinyl-5'-O-[bis(4-methoxyphenoxy)phosphinyl]guanosine;
4'-Vinylguanosine-3',5'-cyclic phosphoric acid isopropyl ester;
3'-Deoxy-3'-fluoro-4'-vinyluridine-5'-(O-1-naphthyl-N—(S)-1-(isopropoxycarbonyl)ethyl phosphoramidate;
3'-Deoxy-3'-fluoro-4'-vinyluridine-5'-(O-1-naphthyl-N—(S)-1-(2,2-dimethylpropoxycarbonyl)ethyl phosphoramidate;
3'-Deoxy-3'-fluoro-4'-vinyluridine-5'-(O-1-naphthyl-N—(S)-1-(benzyloxycarbonyl)ethyl phosphoramidate;
3'-Deoxy-3'-fluoro-4'-vinyluridine-5'-{N,N'-bis[(S)-1-(isopropoxycarbonyl)ethyl]phosphorodiamidate};
3'-Deoxy-3'-fluoro-4'-vinyluridine-5'-{N,N'-bis[(S)-1-(2,2-dimethylpropoxycarbonyl)ethyl]phosphorodiamidate};
3'-Deoxy-3'-fluoro-4'-vinyluridine-5'-{N,N'-bis[(S)-1-(cyclopentoxycarbonyl)ethyl]phosphorodiamidate};
3'-Deoxy-3'-fluoro-4'-vinylcytidine-5'-(O-1-naphthyl-N—(S)-1-(isopropoxycarbonyl)ethyl phosphoramidate;
3'-Deoxy-3'-fluoro-4'-vinylcytidine-5'-(O-1-naphthyl-N—(S)-1-(2,2-dimethylpropoxycarbonyl)ethyl phosphoramidate;
3'-Deoxy-3'-fluoro-4'-vinylcytidine-5'-(O-1-naphthyl-N—(S)-1-(benzyloxycarbonyl)ethyl phosphoramidate;
3'-Deoxy-3'-fluoro-4'-vinylcytidine-5'-{N,N'-bis[(S)-1-(propoxycarbonyl)ethyl]phosphorodiamidate};
3'-Deoxy-3'-fluoro-4'-vinylcytidine-5'-{N,N'-bis[(S)-1-(2,2-dimethylpropoxycarbonyl)ethyl]phosphorodiamidate};
3'-Deoxy-3'-fluoro-4'-vinylcytidine-5'-{N,N'-bis[(S)-1-(hexoxycarbonyl)ethyl]phosphorodiamidate}; and
3'-Deoxy-3'-fluoro-4'-vinylcytidine-5'-{N,N'-bis[(S)-1-(cyclopentoxycarbonyl)ethyl]phosphorodiamidate}.

The application provides a method for preventing or treating an RSV infection comprising administering to a patient in need thereof a therapeutically effective amount of a compound of Formula I.

The application provides the above method, further comprising administering an immune system modulator or an antiviral agent that inhibits replication of RSV, or a combination thereof.

The application provides the above method, wherein the immune system modulator is an RSV vaccine, therapeutic vaccine, adjuvant, an interferon or a chemically derivatized interferon.

The application provides the above method for inhibiting replication of RSV in a cell comprising administering a compound of Formula I.

The application provides a composition comprising the compound of Formula I.

The application provides the above method for inhibiting replication of RSV in a cell comprising administering a composition comprising the compound of Formula I.

The application provides the above composition, admixed with at least one carrier, diluent or excipient.

The application provides a use of the compound of Formula I in the manufacture of a medicament for the treatment of RSV.

The application provides a compound, composition, or method as described herein.

Examples of representative compounds encompassed by the present invention and within the scope of the invention are provided in the following Tables. These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on standard nucleic acid nomenclature common to one of ordinary skill in the art. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE 1

Examples of compounds of generic Formula I.

| Compound Number | Structure | Name |
|---|---|---|
| I-1 | 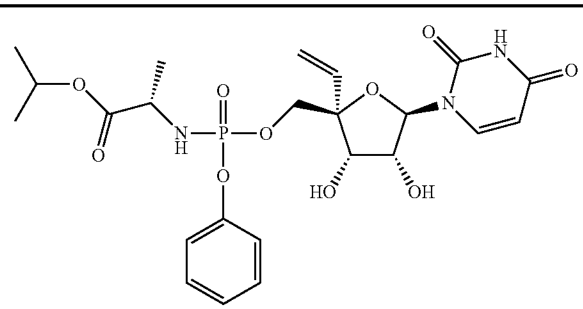 | 4'-Vinyluridine-5'-(O-phenyl-N-(S)-1-(isopropoxycarbonyl)ethyl phosphoramidate |

TABLE 1-continued

Examples of compounds of generic Formula I.

| Compound Number | Structure | Name |
|---|---|---|
| I-2 | 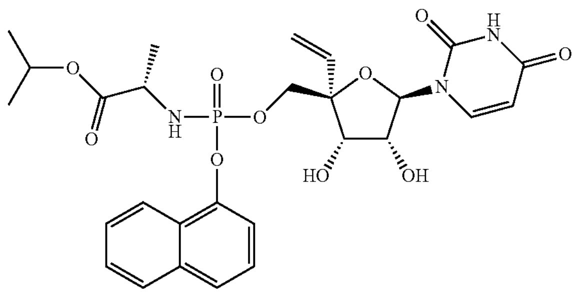 [SMILES: C=C[C@]1(COP(=O)(N[C@@H](C)C(=O)OC(C)C)Oc2cccc3ccccc23)O[C@@H](n2ccc(=O)[nH]c2=O)[C@H](O)[C@@H]1O] | 4'-Vinyluridine-5'-(O-1-naphthyl-N-(S)-1-(isopropoxycarbonyl)ethyl phosphoramidate |
| I-3 | 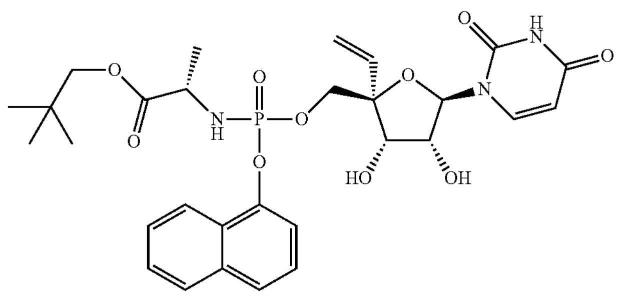 [SMILES: C=C[C@]1(COP(=O)(N[C@@H](C)C(=O)OCC(C)(C)C)Oc2cccc3ccccc23)O[C@@H](n2ccc(=O)[nH]c2=O)[C@H](O)[C@@H]1O] | 4'-Vinyluridine-5'-(O-1-naphthyl-N-(S)-1-(i2,2-dimethylpropoxycarbonyl)ethyl phosphoramidate |
| I-4 | 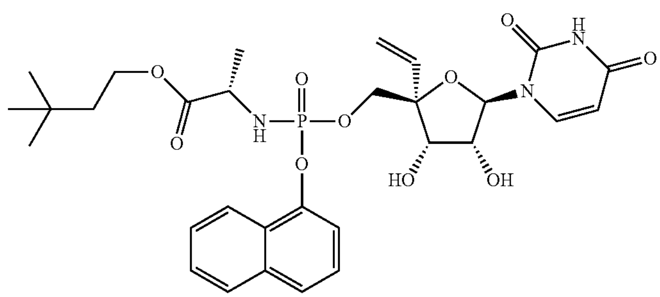 [SMILES: C=C[C@]1(COP(=O)(N[C@@H](C)C(=O)OCCC(C)(C)C)Oc2cccc3ccccc23)O[C@@H](n2ccc(=O)[nH]c2=O)[C@H](O)[C@@H]1O] | 4'-Vinyluridine-5'-(O-1-naphthyl-N-(S)-1-(3,3-dimethylbutoxycarbonyl)ethyl phosphoramidate |
| I-5 | 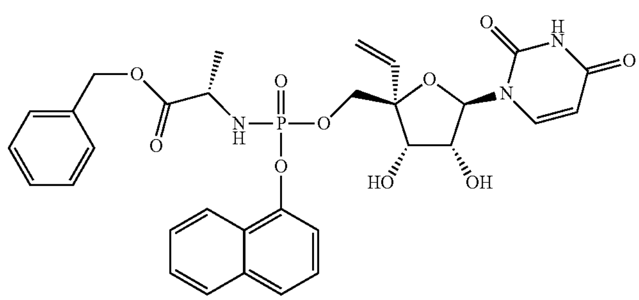 | 4'-Vinyluridine-5'-(O-1-naphthyl-N-(S)-1-(benzyloxycarbonyl)ethyl phosphoramidate |
| I-6 | 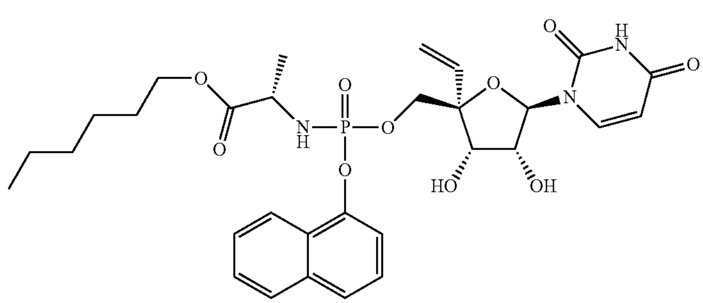 [SMILES: C=C[C@]1(COP(=O)(N[C@@H](C)C(=O)OCCCCCC)Oc2cccc3ccccc23)O[C@@H](n2ccc(=O)[nH]c2=O)[C@H](O)[C@@H]1O] | 4'-Vinyluridine-5'-(O-1-naphthyl-N-(S)-1-(hexoxycarbonyl)ethyl phosphoramidate |

TABLE 1-continued

Examples of compounds of generic Formula I.

| Compound Number | Structure | Name |
| --- | --- | --- |
| I-7 | 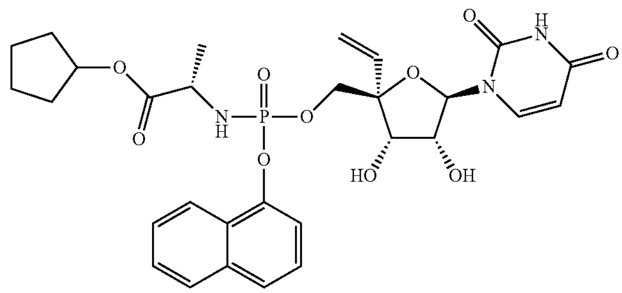 [SMILES: C=C[C@]1(COP(=O)(N[C@@H](C)C(=O)OC2CCCC2)Oc2cccc3ccccc23)O[C@@H](n2ccc(=O)[nH]c2=O)[C@H](O)[C@@H]1O] | 4'-Vinyluridine-5'-(O-1-naphthyl-N-(S)-1-(cyclopentoxycarbonyl)ethyl phosphoramidate |
| I-8 | 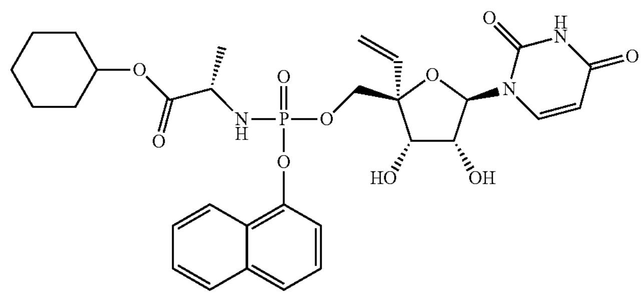 [SMILES: C=C[C@]1(COP(=O)(N[C@@H](C)C(=O)OC2CCCCC2)Oc2cccc3ccccc23)O[C@@H](n2ccc(=O)[nH]c2=O)[C@H](O)[C@@H]1O] | 4'-Vinyluridine-5'-(O-1-naphthyl-N-(S)-1-(cyclohexoxycarbonyl)ethyl phosphoramidate |
| I-9 | 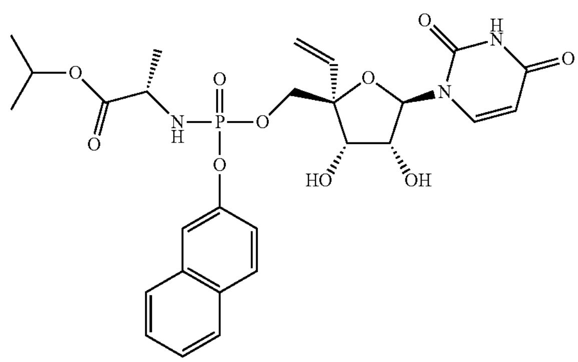 [SMILES: C=C[C@]1(COP(=O)(N[C@@H](C)C(=O)OC(C)C)Oc2ccc3ccccc3c2)O[C@@H](n2ccc(=O)[nH]c2=O)[C@H](O)[C@@H]1O] | 4'-Vinyluridine-5'-(O-2-naphthyl-N-(S)-1-(isopropoxycarbonyl)ethyl phosphoramidate |
| I-10 | 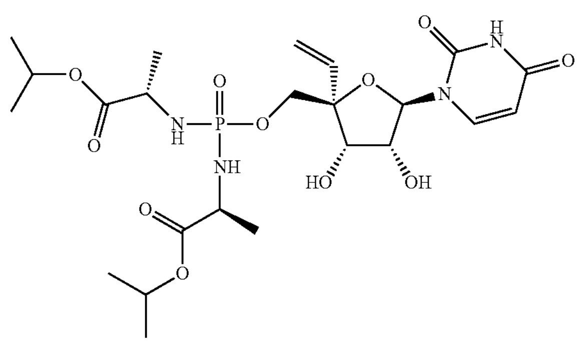 [SMILES: C=C[C@]1(COP(=O)(N[C@@H](C)C(=O)OC(C)C)N[C@@H](C)C(=O)OC(C)C)O[C@@H](n2ccc(=O)[nH]c2=O)[C@H](O)[C@@H]1O] | 4'-Vinyluridine-5'-{N,N'-bis[(S)-1-(isopropoxycarbonyl)ethyl]phosphorodiamidate} |

TABLE 1-continued

Examples of compounds of generic Formula I.

| Compound Number | Structure | Name |
|---|---|---|
| I-11 | 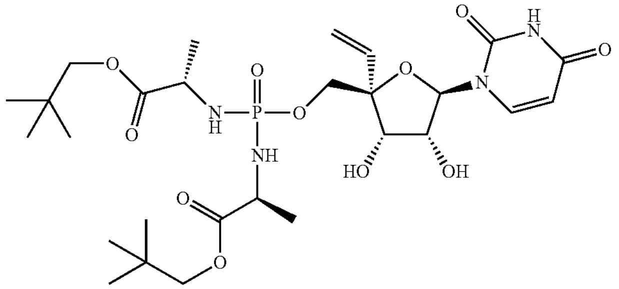 [SMILES: C=C[C@]1(COP(=O)(N[C@@H](C)C(=O)OCC(C)(C)C)N[C@@H](C)C(=O)OCC(C)(C)C)O[C@@H](n2ccc(=O)[nH]c2=O)[C@H](O)[C@@H]1O] | 4'-Vinyluridine-5'-{N,N'-bis[(S)-1-(2,2-dimethylpropoxycarbony)ethyl]phosphorodiamidate} |
| I-12 | 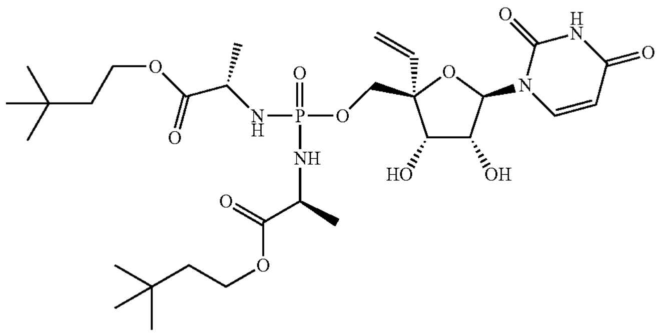 [SMILES: C=C[C@]1(COP(=O)(N[C@@H](C)C(=O)OCCC(C)(C)C)N[C@@H](C)C(=O)OCCC(C)(C)C)O[C@@H](n2ccc(=O)[nH]c2=O)[C@H](O)[C@@H]1O] | 4'-Vinyluridine-5'-{N,N'-bis[(S)-1-(3,3-dimethylbutoxycarbonyl)ethyl]phosphorodiamidate} |
| I-13 | 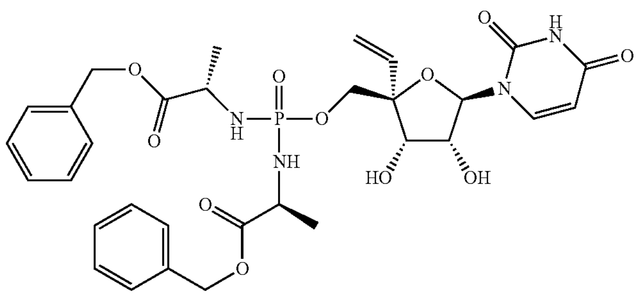 [SMILES: C=C[C@]1(COP(=O)(N[C@@H](C)C(=O)OCc2ccccc2)N[C@@H](C)C(=O)OCc2ccccc2)O[C@@H](n2ccc(=O)[nH]c2=O)[C@H](O)[C@@H]1O] | 4'-Vinyluridine-5'-{N,N'-bis[(S)-1-(benzyloxycarbonyl)ethyl]phosphorodiamidate} |
| I-14 | 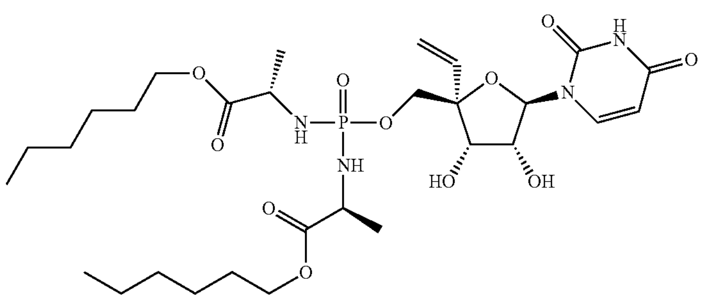 [SMILES: C=C[C@]1(COP(=O)(N[C@@H](C)C(=O)OCCCCCC)N[C@@H](C)C(=O)OCCCCCC)O[C@@H](n2ccc(=O)[nH]c2=O)[C@H](O)[C@@H]1O] | 4'-Vinyluridine-5'-{N,N'-bis[(S)-1-(hexoxycarbonyl)ethyl]phosphorodiamidate} |

TABLE 1-continued

Examples of compounds of generic Formula I.

| Compound Number | Structure | Name |
| --- | --- | --- |
| I-15 | 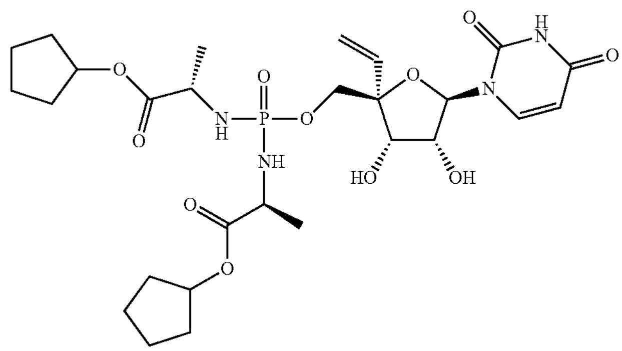 [SMILES: C=C[C@]1(COP(=O)(N[C@@H](C)C(=O)OC2CCCC2)N[C@@H](C)C(=O)OC2CCCC2)O[C@@H](n2ccc(=O)[nH]c2=O)[C@H](O)[C@@H]1O] | 4'-Vinyluridine-5'-{N,N'-bis[(S)-1-(cyclopentoxycarbonyl)ethyl]phosphorodiamidate} |
| I-16 | 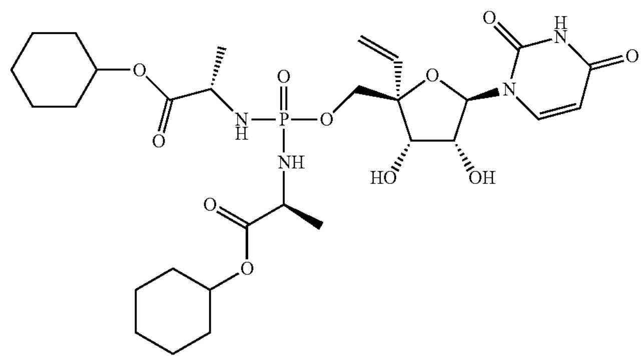 [SMILES: C=C[C@]1(COP(=O)(N[C@@H](C)C(=O)OC2CCCCC2)N[C@@H](C)C(=O)OC2CCCCC2)O[C@@H](n2ccc(=O)[nH]c2=O)[C@H](O)[C@@H]1O] | 4'-Vinyluridine-5'-{N,N'-bis[(S)-1-(cyclohexoxycarbonyl)ethyl]phosphorodiamidate} |
| I-17 | 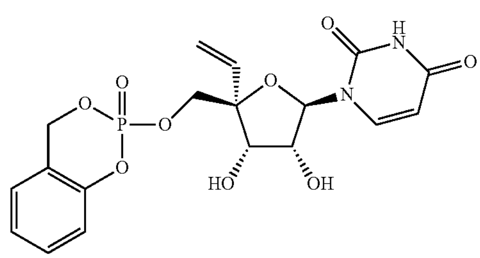 [SMILES: C=C[C@]1(COP2(=O)OCc3ccccc3O2)O[C@@H](n2ccc(=O)[nH]c2=O)[C@H](O)[C@@H]1O] | 4'-Vinyl-5'-O-(2-oxido-4-H-1,3,2-benzodioxaphosphorin-2-yl)-uridine |
| I-18 | 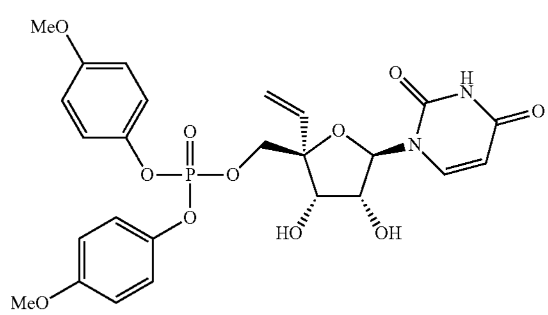 [SMILES: C=C[C@]1(COP(=O)(Oc2ccc(OC)cc2)Oc2ccc(OC)cc2)O[C@@H](n2ccc(=O)[nH]c2=O)[C@H](O)[C@@H]1O] | 4'-Vinyl-5'-O-[bis(4-methoxyphenoxy)phosphinyl]uridine |
| I-19 | 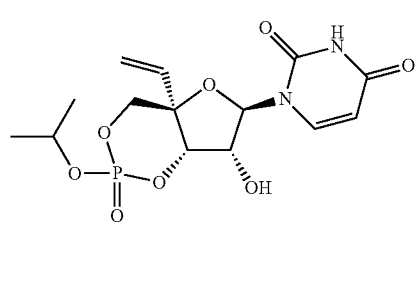 | 4'-Vinyluridine-3',5'-cyclic phosphoric acid isopropyl ester |

TABLE 1-continued

Examples of compounds of generic Formula I.

| Compound Number | Structure | Name |
|---|---|---|
| I-20 | 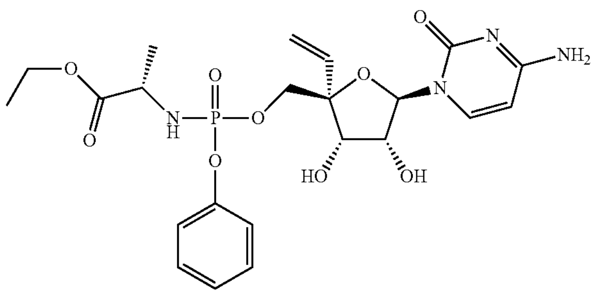 [SMILES: C=C[C@]1(COP(=O)(N[C@@H](C)C(=O)OCC)Oc2ccccc2)O[C@@H](n2ccc(N)nc2=O)[C@H](O)[C@@H]1O] | 4'-Vinylcytidine-5'-(O-phenyl-N-(S)-1-(ethoxycarbonyl)ethyl phosphoramidate |
| I-21 | 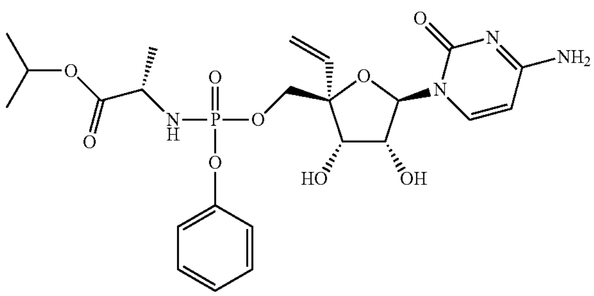 [SMILES: C=C[C@]1(COP(=O)(N[C@@H](C)C(=O)OC(C)C)Oc2ccccc2)O[C@@H](n2ccc(N)nc2=O)[C@H](O)[C@@H]1O] | 4'-Vinylcytidine-5'-(O-phenyl-N-(S)-1-(isopropoxycarbonyl)ethyl phosphoramidate |
| I-22 | 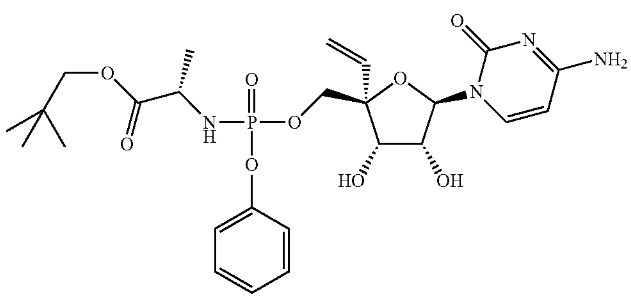 [SMILES: C=C[C@]1(COP(=O)(N[C@@H](C)C(=O)OCC(C)(C)C)Oc2ccccc2)O[C@@H](n2ccc(N)nc2=O)[C@H](O)[C@@H]1O] | 4'-Vinylcytidine-5'-(O-phenyl-N-(S)-1-(neopentoxycarbonyl)ethyl phosphoramidate |
| I-23 | 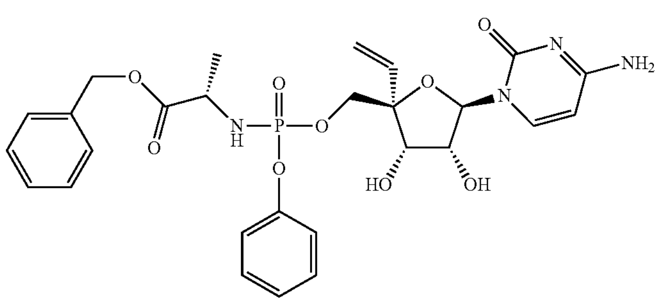 [SMILES: C=C[C@]1(COP(=O)(N[C@@H](C)C(=O)OCc2ccccc2)Oc2ccccc2)O[C@@H](n2ccc(N)nc2=O)[C@H](O)[C@@H]1O] | 4'-Vinylcytidine-5'-(O-phenyl-N-(S)-1-(benzyloxycarbonyl)ethyl phosphoramidate |
| I-24 | 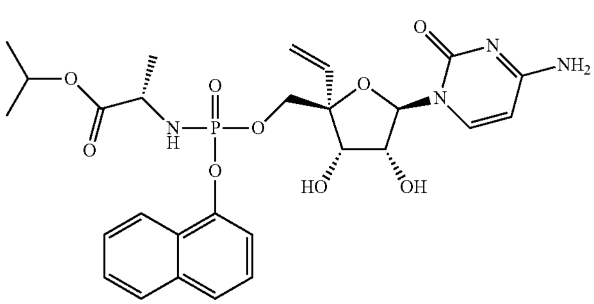 [SMILES: C=C[C@]1(COP(=O)(N[C@@H](C)C(=O)OC(C)C)Oc2cccc3ccccc23)O[C@@H](n2ccc(N)nc2=O)[C@H](O)[C@@H]1O] | 4'-Vinylcytidine-5'-(O-1-naphthyl-N-(S)-1-(isopropoxycarbonyl)ethyl phosphoramidate |

TABLE 1-continued

Examples of compounds of generic Formula I.

| Compound Number | Structure | Name |
|---|---|---|
| I-25 | 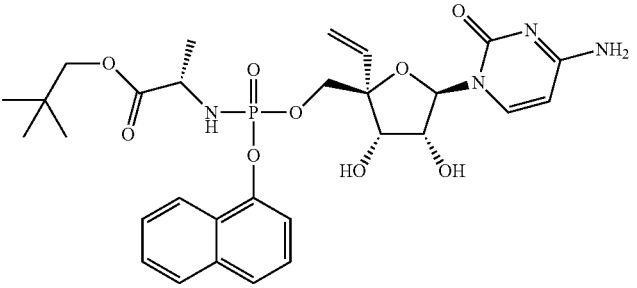 | 4'-Vinylcytidine-5'-(O-1-naphthyl-N-(S)-1-(2,2-dimethylpropoxycarbonyl)ethyl phosphoramidate |
| I-26 | 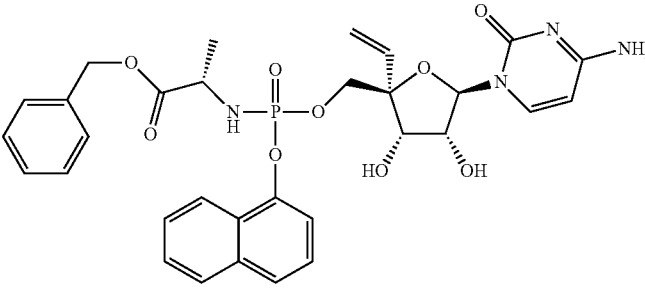 | 4'-Vinylcytidine-5'-(O-1-naphthyl-N-(S)-1-(benzyloxycarbonyl)ethyl phosphoramidate |
| I-27 | 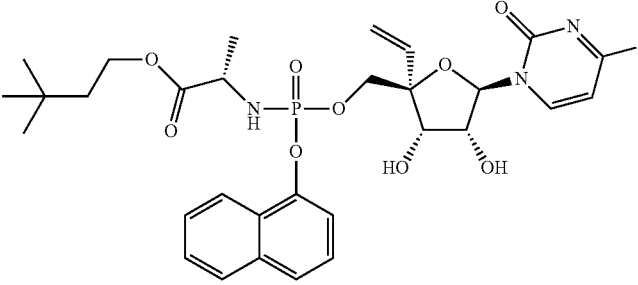 | 4'-Vinylcytidine-5'-(O-1-naphthyl-N-(S)-1-(3,3-dimethybutoxycarbonyl)ethyl phosphoramidate |
| I-28 | 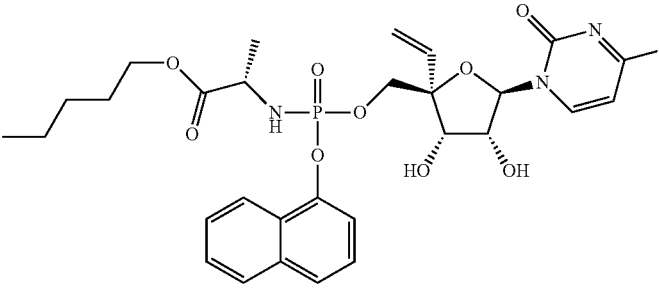 | 4'-Vinylcytidine-5'-(O-1-naphthyl-N-(S)-1-(pentoxycarbonyl)ethyl phosphoramidate |
| I-29 | 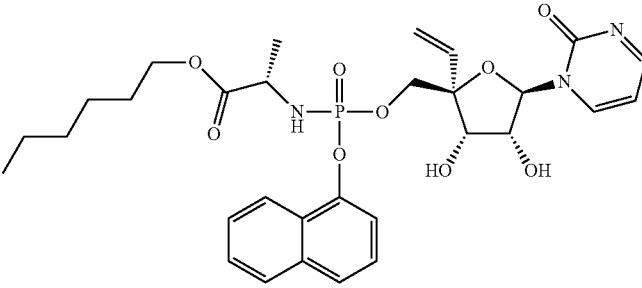 | 4'-Vinylcytidine-5'-(O-1-naphthyl-N-(S)-1-(hexoxycarbonyl)ethyl phosphoramidate |

TABLE 1-continued

Examples of compounds of generic Formula I.

| Compound Number | Structure | Name |
|---|---|---|
| I-30 | 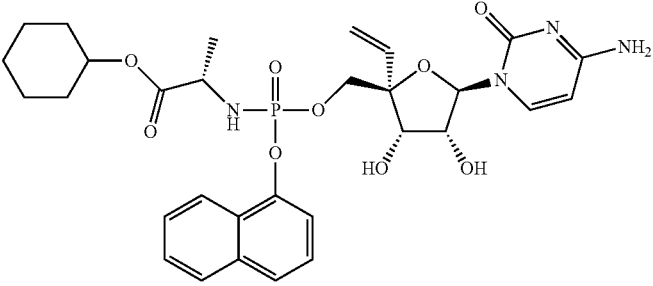 [SMILES: C=C[C@]1(COP(=O)(N[C@@H](C)C(=O)OC2CCCCC2)Oc2cccc3ccccc23)O[C@@H](n2ccc(N)nc2=O)[C@H](O)[C@@H]1O] | 4'-Vinylcytidine-5'-(O-1-naphthyl-N-(S)-1-(cyclohexoxycarbonyl)ethyl phosphoramidate |
| I-31 | 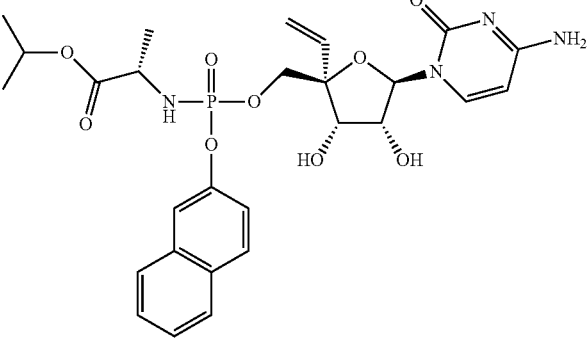 | 4'-Vinylcytidine-5'-(O-2-naphthyl-N-(S)-1-(isopropoxycarbonyl)ethyl phosphoramidate |
| I-32 | 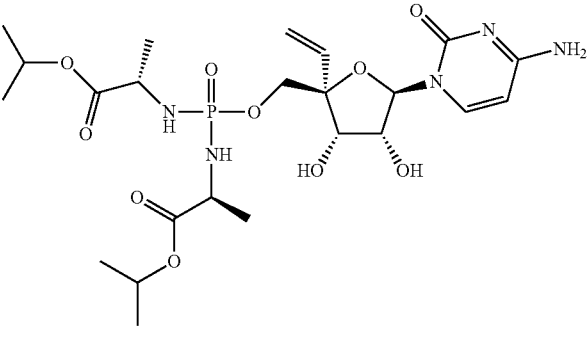 [SMILES: C=C[C@]1(COP(=O)(N[C@@H](C)C(=O)OC(C)C)N[C@@H](C)C(=O)OC(C)C)O[C@@H](n2ccc(N)nc2=O)[C@H](O)[C@@H]1O] | 4'-Vinylcytidine-5'-{N,N'-bis[(S)-1-(isopropoxycarbonyl)ethyl]phosphorodiamidate} |
| I-33 | 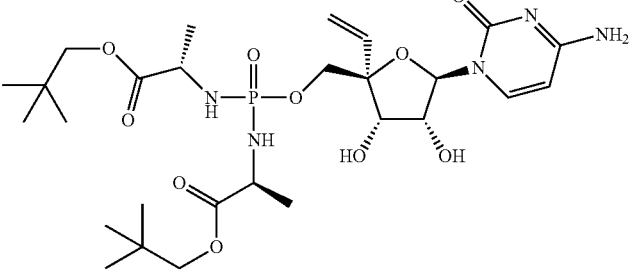 | 4'-Vinylcytidine-5'-{N,N'-bis[(S)-1-(2,2-dimethylpropoxycarbonyl)ethyl]phosphorodiamidate} |

TABLE 1-continued

Examples of compounds of generic Formula I.

| Compound Number | Structure | Name |
|---|---|---|
| I-34 | 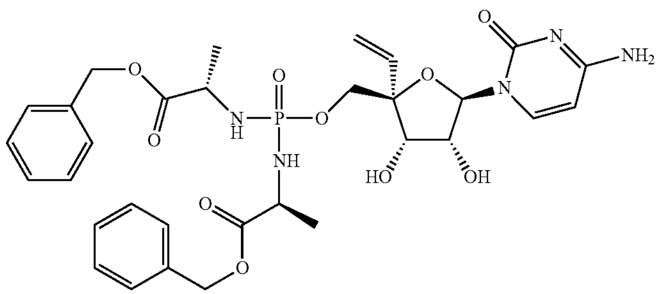 [SMILES: C=C[C@]1(COP(=O)(N[C@@H](C)C(=O)OCc2ccccc2)N[C@@H](C)C(=O)OCc2ccccc2)O[C@@H](n2ccc(N)nc2=O)[C@H](O)[C@@H]1O] | 4'-Vinylcytidine-5'-{N,N'-bis[(S)-1-benzyloxycarbonyl)ethyl]phosphorodiamidate} |
| I-35 | 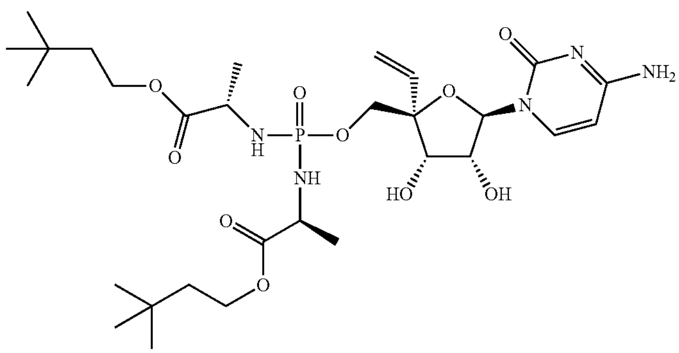 [SMILES: C=C[C@]1(COP(=O)(N[C@@H](C)C(=O)OCCC(C)(C)C)N[C@@H](C)C(=O)OCCC(C)(C)C)O[C@@H](n2ccc(N)nc2=O)[C@H](O)[C@@H]1O] | 4'-Vinylcytidine-5'-{N,N'-bis[(S)-1-(3,3-dimethylbutoxycarbony)ethyl]phosphorodiamidate} |
| I-36 | 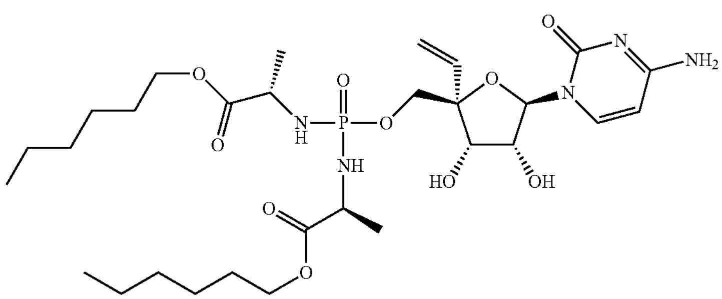 [SMILES: C=C[C@]1(COP(=O)(N[C@@H](C)C(=O)OCCCCCC)N[C@@H](C)C(=O)OCCCCCC)O[C@@H](n2ccc(N)nc2=O)[C@H](O)[C@@H]1O] | 4'-Vinylcytidine-5'-{N,N'-bis[(S)-1-(hexoxycarbonyl)ethyl]phosphorodiamidate} |
| I-37 | 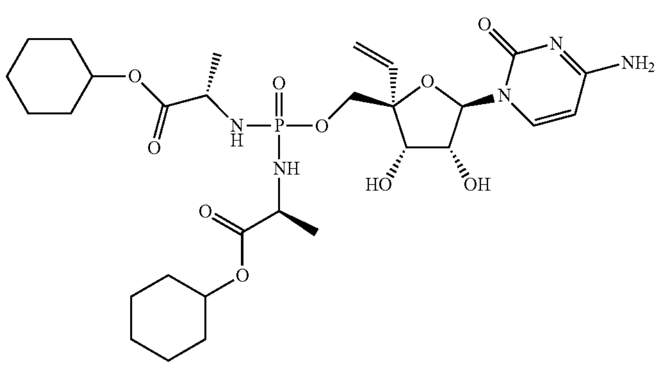 [SMILES: C=C[C@]1(COP(=O)(N[C@@H](C)C(=O)OC2CCCCC2)N[C@@H](C)C(=O)OC2CCCCC2)O[C@@H](n2ccc(N)nc2=O)[C@H](O)[C@@H]1O] | 4'-Vinylcytidine-5'-{N,N'-bis[(S)-1-(cyclohexoxycarbonyl)ethyl]phosphorodiamidate} |
| I-38 | 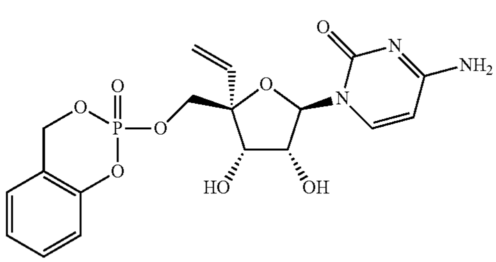 [SMILES: C=C[C@]1(COP2(=O)OCc3ccccc3O2)O[C@@H](n2ccc(N)nc2=O)[C@H](O)[C@@H]1O] | 4'-Vinyl-5'-O-(2-oxido-4-H-1,3,2-benzodioxaphosphorin-2-yl)-cytidine |

TABLE 1-continued

Examples of compounds of generic Formula I.

| Compound Number | Structure | Name |
|---|---|---|
| I-39 | 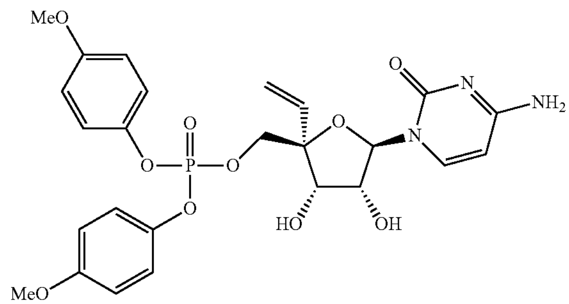 [SMILES: C=C[C@]1(COP(=O)(Oc2ccc(OC)cc2)Oc2ccc(OC)cc2)O[C@@H](n2ccc(N)nc2=O)[C@H](O)[C@@H]1O] | 4'-Vinyl-5'-O-[bis(4-methoxyphenoxy)phosphinyl] cytidine |
| I-40 | 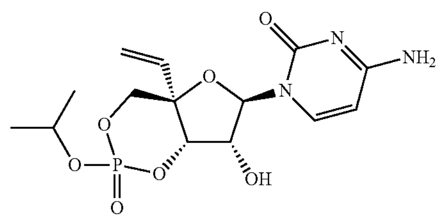 | 4'-Vinylcytidine-3',5'-cyclic phosphoric acid isopropyl ester |
| I-41 | 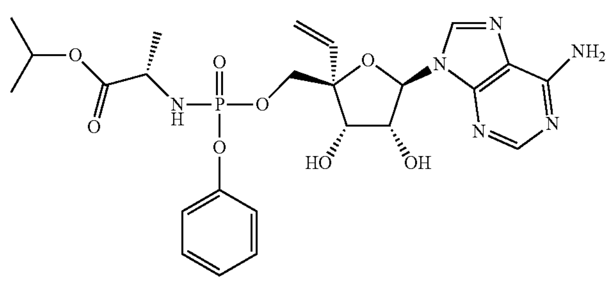 [SMILES: C=C[C@]1(COP(=O)(N[C@@H](C)C(=O)OC(C)C)Oc2ccccc2)O[C@@H](n2cnc3c(N)ncnc32)[C@H](O)[C@@H]1O] | 4'-Viyladenosine-5'-(O-phenyl-N-(S)-1-(isopropoxycarbonyl)ethyl phosphoramidate |
| I-42 | 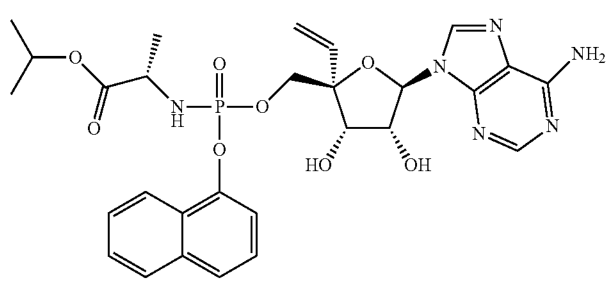 [SMILES: C=C[C@]1(COP(=O)(N[C@@H](C)C(=O)OC(C)C)Oc2cccc3ccccc23)O[C@@H](n2cnc3c(N)ncnc32)[C@H](O)[C@@H]1O] | 4'-Vinyladenosine-5'-(O-1-naphthyl-N-(S)-1-(isopropoxycarbonyl)ethyl phosphoramidate |
| I-43 | 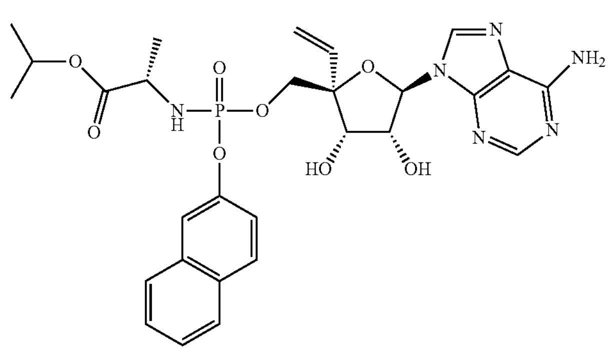 [SMILES: C=C[C@]1(COP(=O)(N[C@@H](C)C(=O)OC(C)C)Oc2ccc3ccccc3c2)O[C@@H](n2cnc3c(N)ncnc32)[C@H](O)[C@@H]1O] | 4'-Vinyladenosine-5'-(O-2-naphthyl-N-(S)-1-(isopropoxycarbonyl)ethyl phosphoramidate |

TABLE 1-continued

Examples of compounds of generic Formula I.

| Compound Number | Structure | Name |
|---|---|---|
| I-44 | 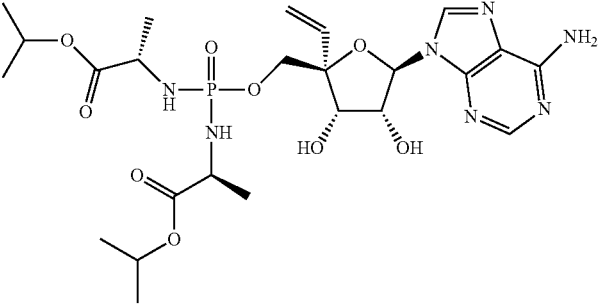 [SMILES: C=C[C@]1(COP(=O)(N[C@@H](C)C(=O)OC(C)C)N[C@@H](C)C(=O)OC(C)C)O[C@@H](n2cnc3c(N)ncnc32)[C@H](O)[C@@H]1O] | 4'-Vinyladenosine-5'-{N,N'-bis[(S)-1-isopropoxycarbonyl)ethyl]phosphorodiamidate |
| I-45 | 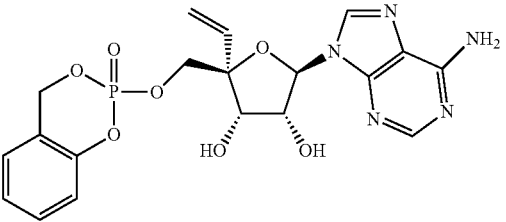 [SMILES: C=C[C@]1(COP2(=O)OCc3ccccc3O2)O[C@@H](n2cnc3c(N)ncnc32)[C@H](O)[C@@H]1O] | 4'-Vinyl-5'-O-(2-oxido-4-H-1,3,2-benzodioxaphosphorin-2-yl)-adenosine |
| I-46 | 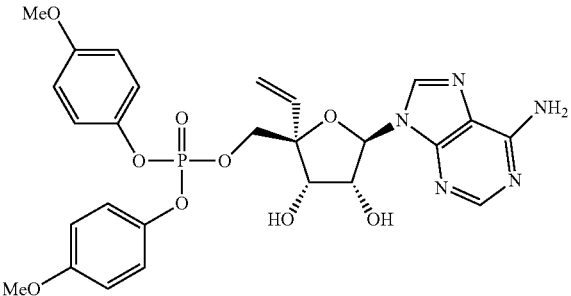 [SMILES: C=C[C@]1(COP(=O)(Oc2ccc(OC)cc2)Oc2ccc(OC)cc2)O[C@@H](n2cnc3c(N)ncnc32)[C@H](O)[C@@H]1O] | 4'-Vinyl-5'-O-[bis(4-methoxyphenoxy)phosphinyl]adenosine |
| I-47 | 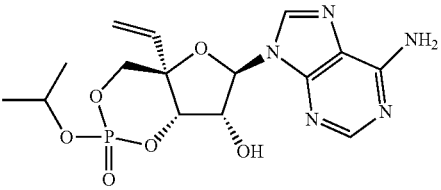 | 4'-Vinyladenosine-3',5'-cyclic acid isopropyl ester |
| I-48 | 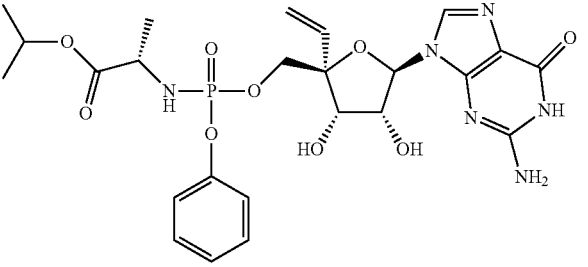 [SMILES: C=C[C@]1(COP(=O)(N[C@@H](C)C(=O)OC(C)C)Oc2ccccc2)O[C@@H](n2cnc3c(=O)[nH]c(N)nc32)[C@H](O)[C@@H]1O] | 4'-Vinylguanosine-5'-(O-phenyl-N-(S)-1-(isopropoxycarbonyl)ethyl phosphoramidate |

TABLE 1-continued

Examples of compounds of generic Formula I.

| Compound Number | Structure | Name |
| --- | --- | --- |
| I-49 | 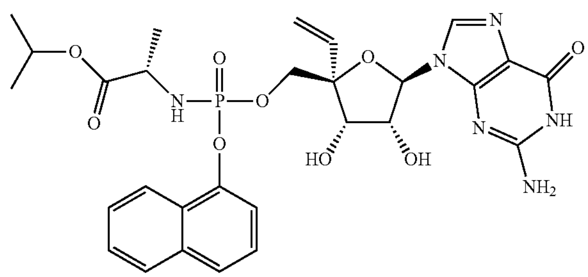 [SMILES: C=C[C@]1(COP(=O)(N[C@@H](C)C(=O)OC(C)C)Oc2cccc3ccccc23)O[C@@H](n2cnc3c(=O)[nH]c(N)nc32)[C@H](O)[C@@H]1O] | 4'-Vinylguanosine-5'-(O-1-naphthyl-N-(S)-1-(isopropoxycarbonyl)ethyl phosphoramidate |
| I-50 | 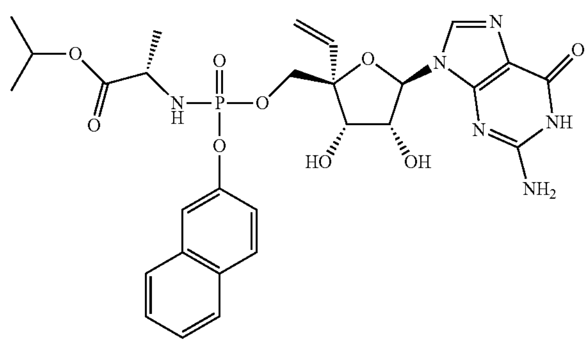 [SMILES: C=C[C@]1(COP(=O)(N[C@@H](C)C(=O)OC(C)C)Oc2ccc3ccccc3c2)O[C@@H](n2cnc3c(=O)[nH]c(N)nc32)[C@H](O)[C@@H]1O] | 4'-Vinylguanosine-5'-(O-2-naphthyl-N-(S)-1-(isopropoxycarbonyl)ethyl phosphoramidate |
| I-51 | 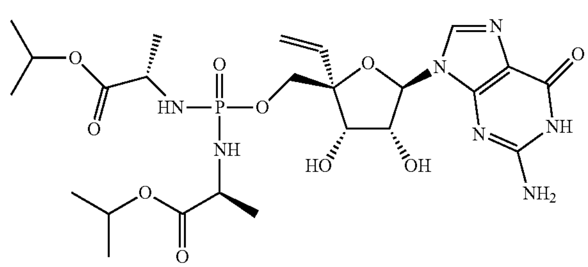 [SMILES: C=C[C@]1(COP(=O)(N[C@@H](C)C(=O)OC(C)C)N[C@@H](C)C(=O)OC(C)C)O[C@@H](n2cnc3c(=O)[nH]c(N)nc32)[C@H](O)[C@@H]1O] | 4'-Vinylguanosine-5'-{N,N'-bis[(S)-1-(isopropoxycarbonyl)ethyl]phosphorodiamidate |
| I-52 | 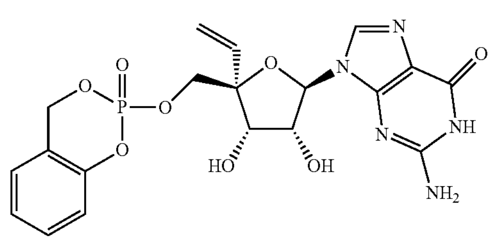 [SMILES: C=C[C@]1(COP2(=O)OCc3ccccc3O2)O[C@@H](n2cnc3c(=O)[nH]c(N)nc32)[C@H](O)[C@@H]1O] | 4'-Vinyl-5'-O-(2-oxido-4-H-1,3,2-benzodioxaphosphorin-2-yl)-guanosine |
| I-53 | 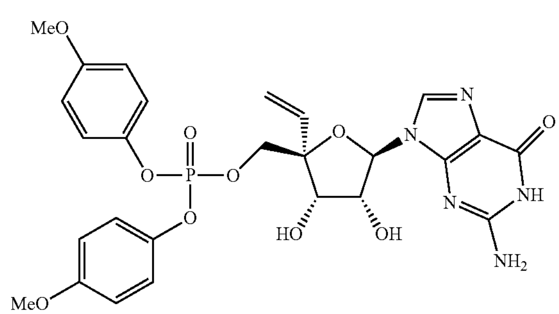 [SMILES: C=C[C@]1(COP(=O)(Oc2ccc(OC)cc2)Oc2ccc(OC)cc2)O[C@@H](n2cnc3c(=O)[nH]c(N)nc32)[C@H](O)[C@@H]1O] | 4'-Vinyl-5'-O-[bis(4-methoxyphenoxy)phosphinyl]guanosine |

TABLE 1-continued

Examples of compounds of generic Formula I.

| Compound Number | Structure | Name |
|---|---|---|
| I-54 | 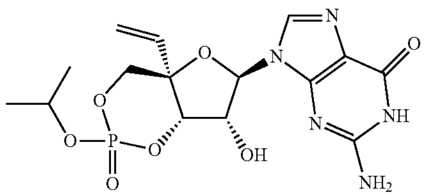 | 4'-Vinylguanosine-3',5'-cyclic phosphoric acid isopropyl ester |
| I-55 | 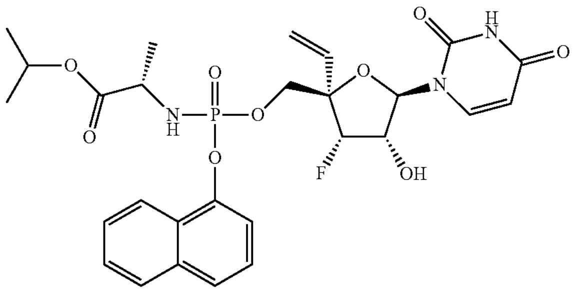 [SMILES: C=C[C@]1(COP(=O)(N[C@@H](C)C(=O)OC(C)C)Oc2cccc3ccccc23)O[C@@H](n2ccc(=O)[nH]c2=O)[C@H](O)[C@@H]1F] | 3'-Deoxy-3'-fluoro-4'-vinyluridine-5'-(O-1-naphthyl-N-(S)-1-(isopropoxycarbonyl)ethyl phosphoramidate |
| I-56 | 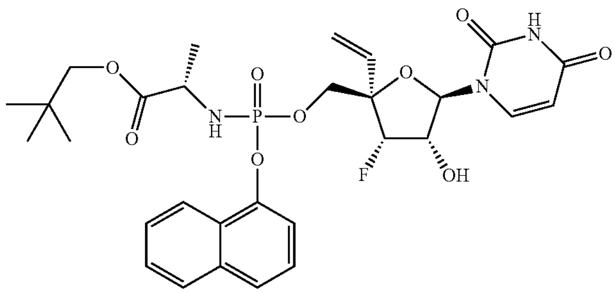 [SMILES: C=C[C@]1(COP(=O)(N[C@@H](C)C(=O)OCC(C)(C)C)Oc2cccc3ccccc23)O[C@@H](n2ccc(=O)[nH]c2=O)[C@H](O)[C@@H]1F] | 3'-Deoxy-3'-fluoro-4'-vinyluridine-5'-(O-1-naphthyl-N-(S)-1-(2,2-dimethylpropoxycarbonyl)ethyl phosphoramidate |
| I-57 | 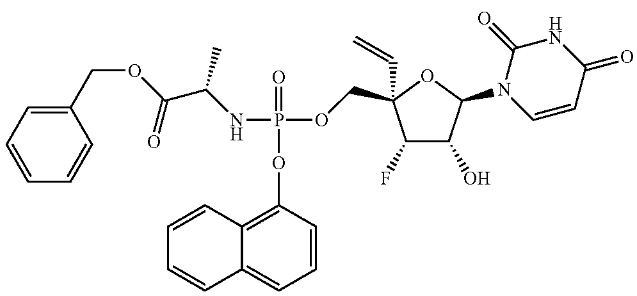 [SMILES: C=C[C@]1(COP(=O)(N[C@@H](C)C(=O)OCc2ccccc2)Oc2cccc3ccccc23)O[C@@H](n2ccc(=O)[nH]c2=O)[C@H](O)[C@@H]1F] | 3'-Deoxy-3'-fluoro-4'-vinyluridine-5'-(O-1-naphthyl-N-(S)-1-(benzyloxycarbonyl)ethyl phosphoramidate |
| I-58 | 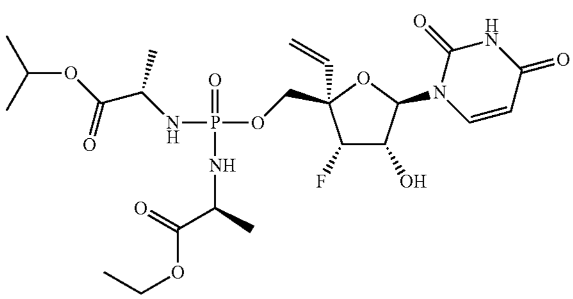 [SMILES: C=C[C@]1(COP(=O)(N[C@@H](C)C(=O)OCC)N[C@@H](C)C(=O)OC(C)C)O[C@@H](n2ccc(=O)[nH]c2=O)[C@H](O)[C@@H]1F] | 3'-Deoxy-3'-fluoro-4'-vinyluridine-5'-{N,N'-bis[(S)-1-(isopropoxycarbonyl)ethyl]phosphorodiamidate} |

TABLE 1-continued

Examples of compounds of generic Formula I.

| Compound Number | Structure | Name |
|---|---|---|
| I-59 | 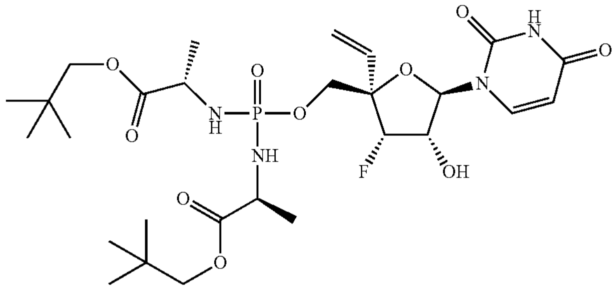 [SMILES: C=C[C@]1(COP(=O)(N[C@@H](C)C(=O)OCC(C)(C)C)N[C@@H](C)C(=O)OCC(C)(C)C)O[C@@H](n2ccc(=O)[nH]c2=O)[C@H](O)[C@@H]1F] | 3'-Deoxy-3'-fluoro-4'-vinyluridine-5'-{N,N'-bis[(S)-1-(2,2-dimethylpropoxycarbonyl)ethyl]phosphorodiamidate} |
| I-60 | 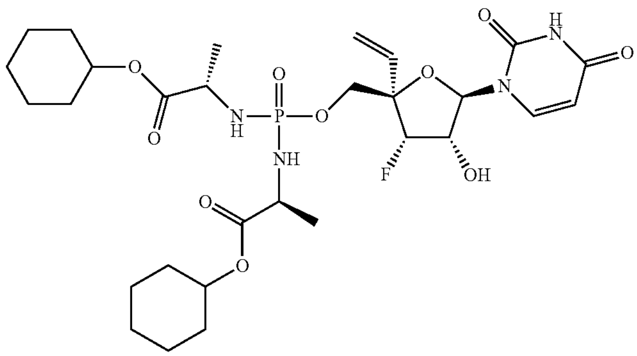 [SMILES: C=C[C@]1(COP(=O)(N[C@@H](C)C(=O)OC2CCCCC2)N[C@@H](C)C(=O)OC2CCCCC2)O[C@@H](n2ccc(=O)[nH]c2=O)[C@H](O)[C@@H]1F] | 3'-Deoxy-3'-fluoro-4'-vinyluridine-5'-{N,N'-bis[(S)-1-(cyclopentoxycarbonyl)ethyl]phosphorodiamidate} |
| I-61 | 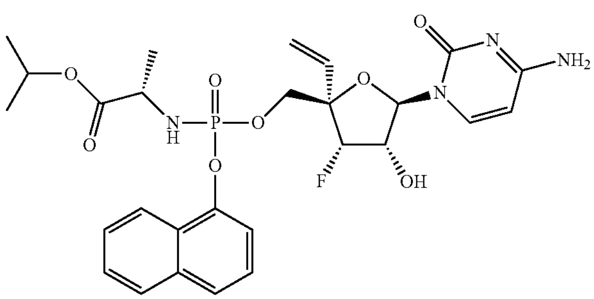 [SMILES: C=C[C@]1(COP(=O)(N[C@@H](C)C(=O)OC(C)C)Oc2cccc3ccccc23)O[C@@H](n2ccc(N)nc2=O)[C@H](O)[C@@H]1F] | 3'-Deoxy-3'-fluoro-4'-vinylcytidine-5'-(O-1-naphthyl-N-(S)-1-(isopropoxycarbonyl)ethyl phosphoramidate |
| I-62 | 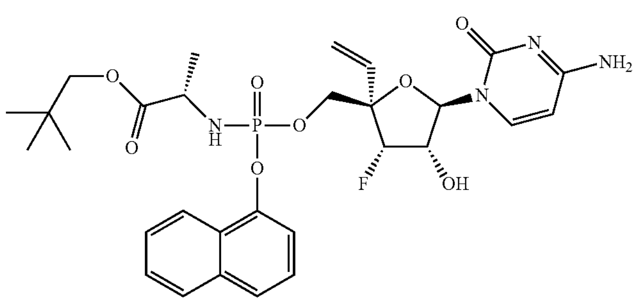 [SMILES: C=C[C@]1(COP(=O)(N[C@@H](C)C(=O)OCC(C)(C)C)Oc2cccc3ccccc23)O[C@@H](n2ccc(N)nc2=O)[C@H](O)[C@@H]1F] | 3'-Deoxy-3'-fluoro-4'-vinylcytidine-5'-(O-1-naphthyl-N-(S)-1-(2,2-dimethylpropoxycarbonyl)ethyl phosphoramidate |
| I-63 | 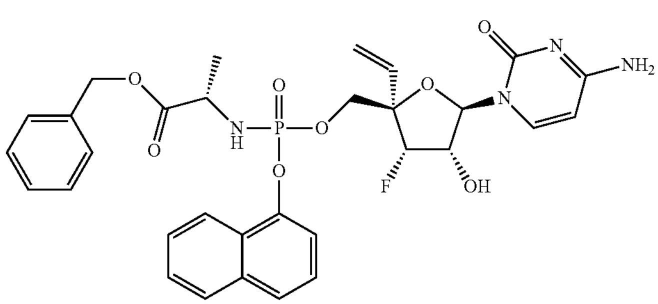 [SMILES: C=C[C@]1(COP(=O)(N[C@@H](C)C(=O)OCc2ccccc2)Oc2cccc3ccccc23)O[C@@H](n2ccc(N)nc2=O)[C@H](O)[C@@H]1F] | 3'-Deoxy-3'-fluoro-4'-vinylcytidine-5'-(O-1-naphthyl-N-(S)-1-(benzyloxycarbonyl)ethyl phosphoramidate |

TABLE 1-continued

Examples of compounds of generic Formula I.

| Compound Number | Structure | Name |
|---|---|---|
| I-64 | 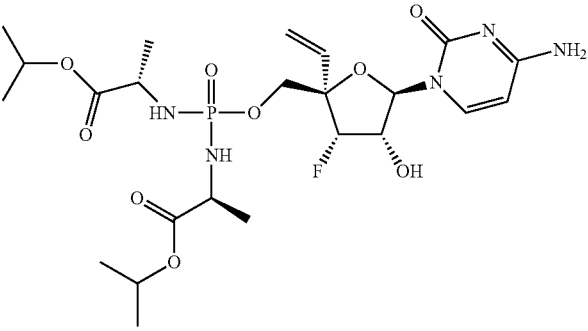 [SMILES: C=C[C@]1(COP(=O)(N[C@@H](C)C(=O)OC(C)C)N[C@@H](C)C(=O)OC(C)C)O[C@@H](n2ccc(N)nc2=O)[C@H](O)[C@@H]1F] | 3'-Deoxy-3'-fluoro-4'-vinylcytidine-5'-{N,N'-bis[(S)-1-(propoxycarbonyl)ethyl]phosphorodiamidate} |
| I-65 | 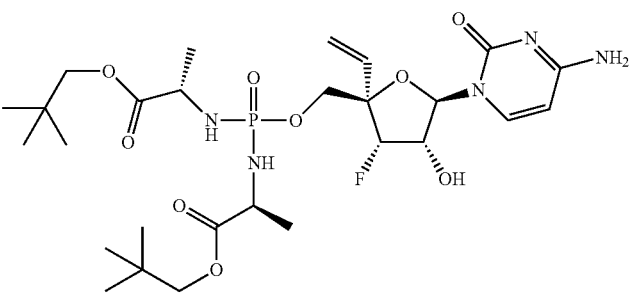 [SMILES: C=C[C@]1(COP(=O)(N[C@@H](C)C(=O)OCC(C)(C)C)N[C@@H](C)C(=O)OCC(C)(C)C)O[C@@H](n2ccc(N)nc2=O)[C@H](O)[C@@H]1F] | 3'-Deoxy-3'-fluoro-4'-vinylcytidine-5'-{N,N'-bis[(S)-1-(2,2-dimethylpropoxycarbonyl)ethyl]phosphorodiamidate} |
| I-66 | 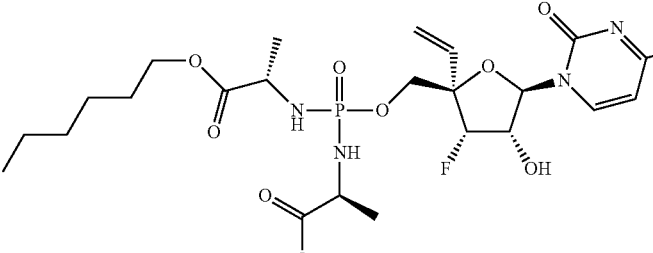 | 3'-Deoxy-3'-fluoro-4'-vinylcytidine-5'-{N,N'-bis[(S)-1-(hexoxycarbonyl)ethyl]phosphorodiamidate} |
| I-67 | 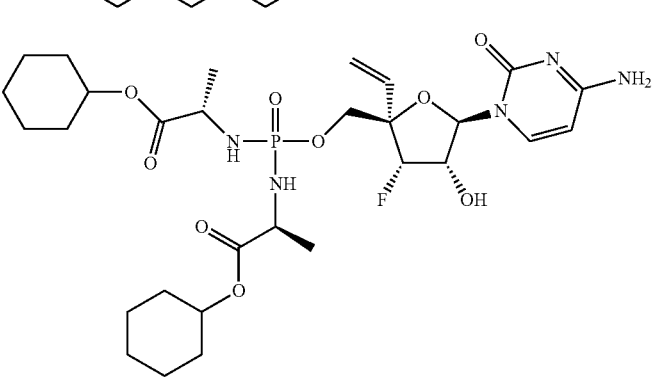 | 3'-Deoxy-3'-fluoro-4'-vinylcytidine-5'-{N,N'-bis[(S)-1-(cyclopentoxycarbonyl)ethyl]phosphorodiamidate} |

Examples

Abbreviations used in this application include: acetyl (Ac), acetic acid (HOAc), azo-bis-isobutyrylnitrile (AIBN), 1-N-hydroxybenzotriazole (HOBt), atmospheres (Atm), high pressure liquid chromatography (HPLC), 9-borabicyclo[3.3.1]nonane (9-BBN or BBN), methyl (Me), tert-butoxycarbonyl (Boc), acetonitrile (MeCN), di-tert-butyl pyrocarbonate or boc anhydride ($BOC_2O$), 1-(3-dimethylaminopropyl)-3-ethylcarbodiimide hydrochloride (EDCI), benzoyl (Bz), benzyl (Bn), m-chloroperbenzoic acid (MCPBA), butyl (Bu), methanol (MeOH), benzyloxycarbonyl (cbz or Z), melting point (mp), carbonyl diimidazole (CDI), $MeSO_2$— (mesyl or Ms), 1,4-diazabicyclo[2.2.2]octane (DABCO), mass spectrum (ms) diethylaminosulfur trifluoride (DAST), methyl t-butyl ether (MTBE), dibenzylideneacetone (Dba), N-carboxyanhydride (NCA), 1,5-diazabicyclo[4.3.0]non-5-ene (DBN), N-bromosuccinimide (NBS), 1,8-diazabicyclo[5.4.0]undec-7-ene (DBU), N-methylmorpholine (NMM), N-methylpyrrolidone (NMP), 1,2-dichloroethane (DCE), pyridinium chlorochromate (PCC), N,N'-dicyclohexylcarbodiimide (DCC), pyridinium dichromate (PDC), dichloromethane (DCM), propyl (Pr), diethyl azodicarboxylate (DEAD), phenyl (Ph), di-isopropylazodicarboxylate, DIAD, pounds per square inch (psi), di-iso-propylethylamine (DIPEA), pyridine (pyr), di-iso-butylaluminumhydride, DIBAL-H, room temperature, rt or RT, N,N-dimethyl acetamide (DMA), tert-butyldimethylsilyl or t-BuMe$_2$Si, (TBDMS), 4-N,N-dimethylaminopyridine (DMAP), triethylamine (Et$_3$N or TEA), N,N-dimethylformamide (DMF), triflate or CF$_3$SO$_2$— (Tf), dimethyl sulfoxide (DMSO), trifluoroacetic acid (TFA), 1,1'-bis-(diphenylphosphino)ethane (dppe), 2,2,6,6-tetramethylheptane-2,6-dione (TMHD), 1,1'-bis-(diphenylphosphino)ferrocene (dppf), thin layer chromatography (TLC), ethyl acetate (EtOAc), tetrahydrofuran (THF), diethyl ether (Et$_2$O), trimethylsilyl or Me$_3$Si (TMS), ethyl (Et), p-toluenesulfonic acid monohydrate (TsOH or pTsOH), lithium hexamethyl disilazane (LiHMDS), 4-Me-C$_6$H$_4$SO$_2$— or tosyl (Ts), iso-propyl (i-Pr), N-urethane-N-carboxyanhydride (UNCA), ethanol (EtOH). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford.).

General Conditions

Compounds of the invention can be made by a variety of methods depicted in the illustrative synthetic reactions described below in the Examples section.

The starting materials and reagents used in preparing these compounds generally are either available from commercial suppliers, such as Aldrich Chemical Co., or are prepared by methods known to those skilled in the art following procedures set forth in references such as Fieser and Fieser's *Reagents for Organic Synthesis*; Wiley & Sons: New York, 1991, Volumes 1-15; Rodd's *Chemistry of Carbon Compounds*, Elsevier Science Publishers, 1989, Volumes 1-5 and Supplementals; and *Organic Reactions*, Wiley & Sons: New York, 1991, Volumes 1-40. It should be appreciated that the synthetic reaction schemes shown in the Examples section are merely illustrative of some methods by which the compounds of the invention can be synthesized, and various modifications to these synthetic reaction schemes can be made and will be suggested to one skilled in the art having referred to the disclosure contained in this application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein are typically conducted under an inert atmosphere at atmospheric pressure at a reaction temperature range of from about −78° C. to about 150° C., often from about 0° C. to about 125° C., and more often and conveniently at about room (or ambient) temperature, e.g., about 20° C.

Various substituents on the compounds of the invention can be present in the starting compounds, added to any one of the intermediates or added after formation of the final products by known methods of substitution or conversion reactions. If the substituents themselves are reactive, then the substituents can themselves be protected according to the techniques known in the art. A variety of protecting groups are known in the art, and can be employed. Examples of many of the possible groups can be found in "*Protective Groups in Organic Synthesis*" by Green et al., John Wiley and Sons, 1999. For example, nitro groups can be added by nitration and the nitro group can be converted to other groups, such as amino by reduction, and halogen by diazotization of the amino group and replacement of the diazo group with halogen. Acyl groups can be added by Friedel-Crafts acylation. The acyl groups can then be transformed to the corresponding alkyl groups by various methods, including the Wolff-Kishner reduction and Clemmenson reduction. Amino groups can be alkylated to form mono- and di-alkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product, including isolated products.

The starting material of type 1 was prepared according to the literature (*J. Med. Chem.*, 2000, 43, 4516) and converted to the vinyl derivative 2 by Wittig reaction. Deprotection and acetolysis provide 3 that underwent Vorbrüggen reaction to the cytidine analogue 4. Further deprotection by ammonia followed by boron trichloride provided 4'-vinylcytidine 6 (Scheme 1).

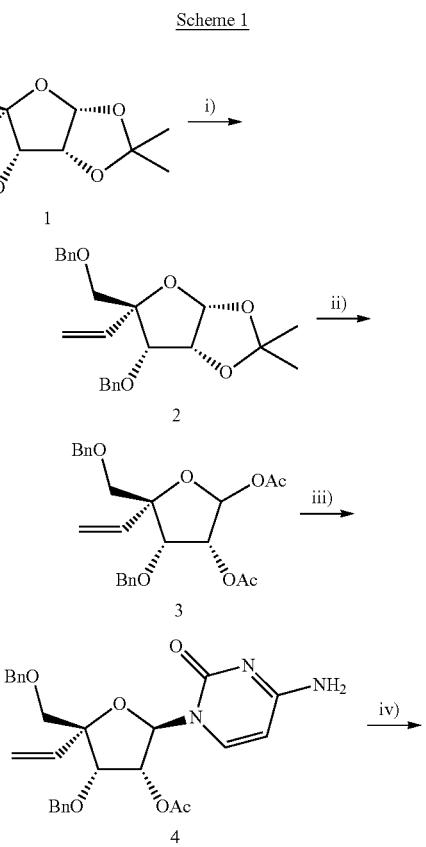

Scheme 1

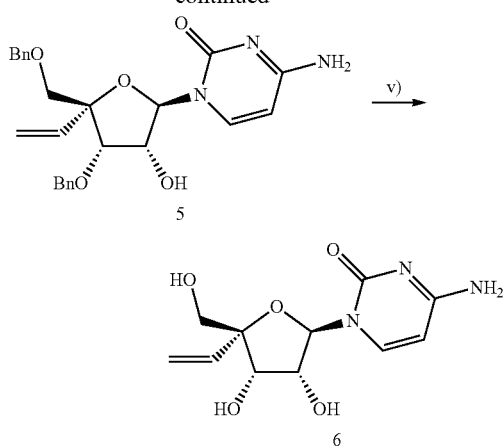

i) PPh₃CH₃I, BuLi, THF; ii) AcOH, Ac₂O, H₂SO₄; iii) Cytosine, BSA, SnCl₄, MeCN; iv) NH₃·H₂O, Dioxane; v) BCl₃, Pyriine 4′-Vinyluridine was synthesized according to the procedure outlined in Scheme 2. 4′-Vinylcytidine 6 was converted to the corresponding phosphoramidates of type 12 according to the procedure in Scheme 3. Compounds of type 15 are prepared according to the standard procedure outlined in Scheme 4.

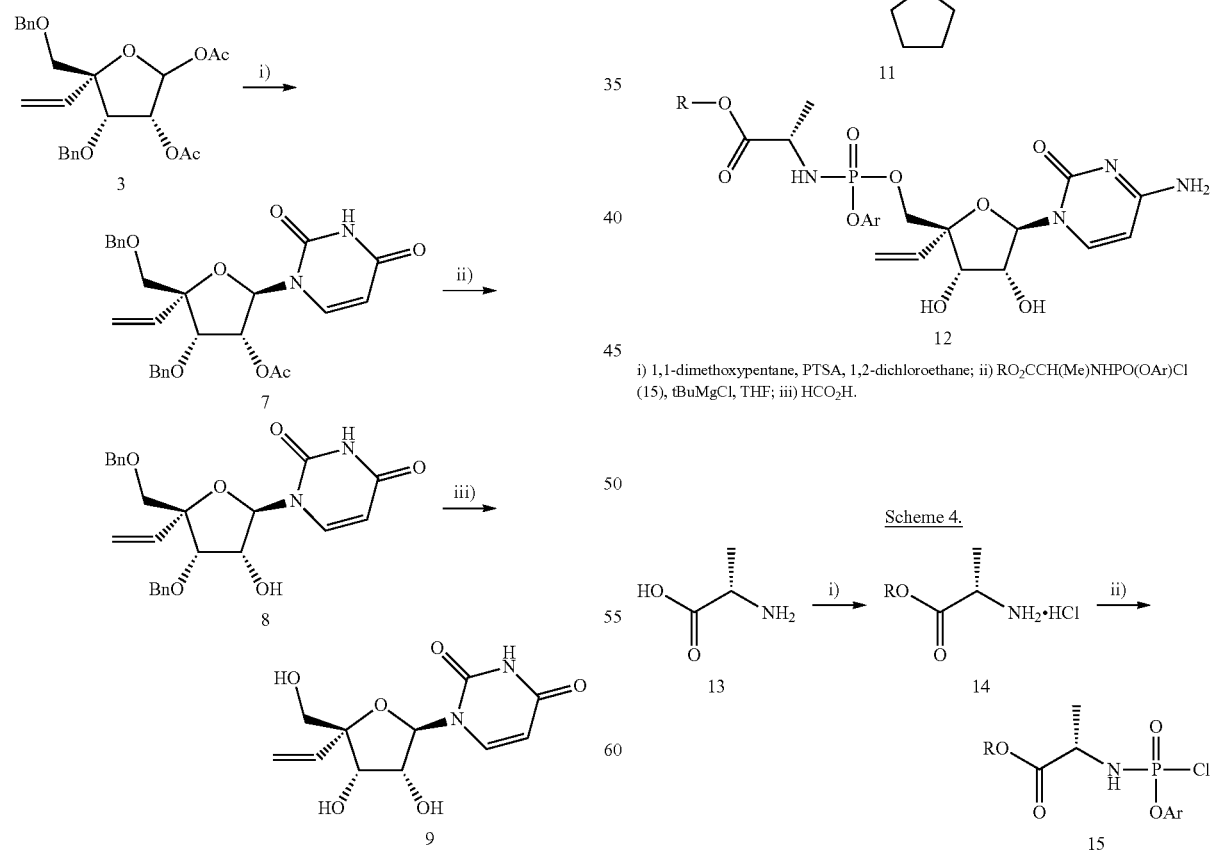

i) Uracil, BSA, SnCl₄, MeCN; ii) NH₃·H₂O, Dioxane; iii) BCl₃, Pyriine

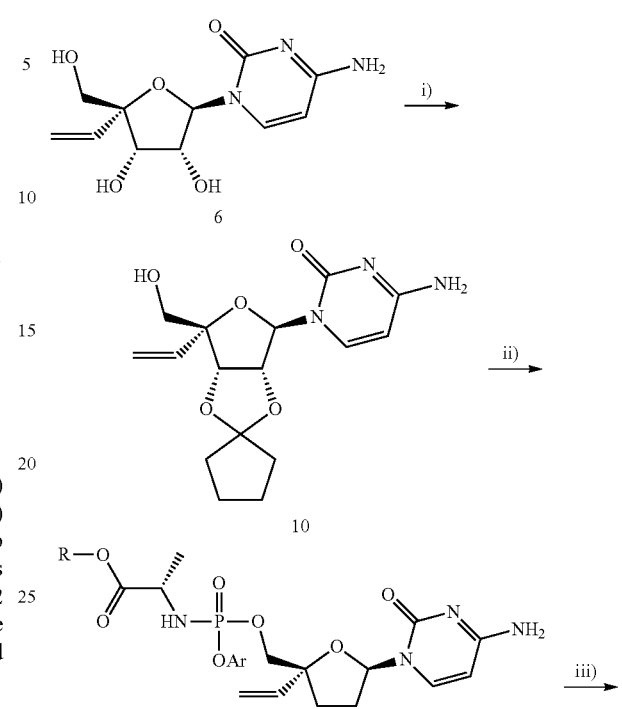

i) 1,1-dimethoxypentane, PTSA, 1,2-dichloroethane; ii) RO₂CCH(Me)NHPO(OAr)Cl (15), tBuMgCl, THF; iii) HCO₂H.

i) SOCl₂, ROH; ii) ArOP(O)Cl₂, Et₃N, CH₂Cl₂

3'-Deoxy-3'-fluoro-4'-vinyl nucleosides of type 26 should be readily prepared as outlined in Scheme 5.

Scheme 5.

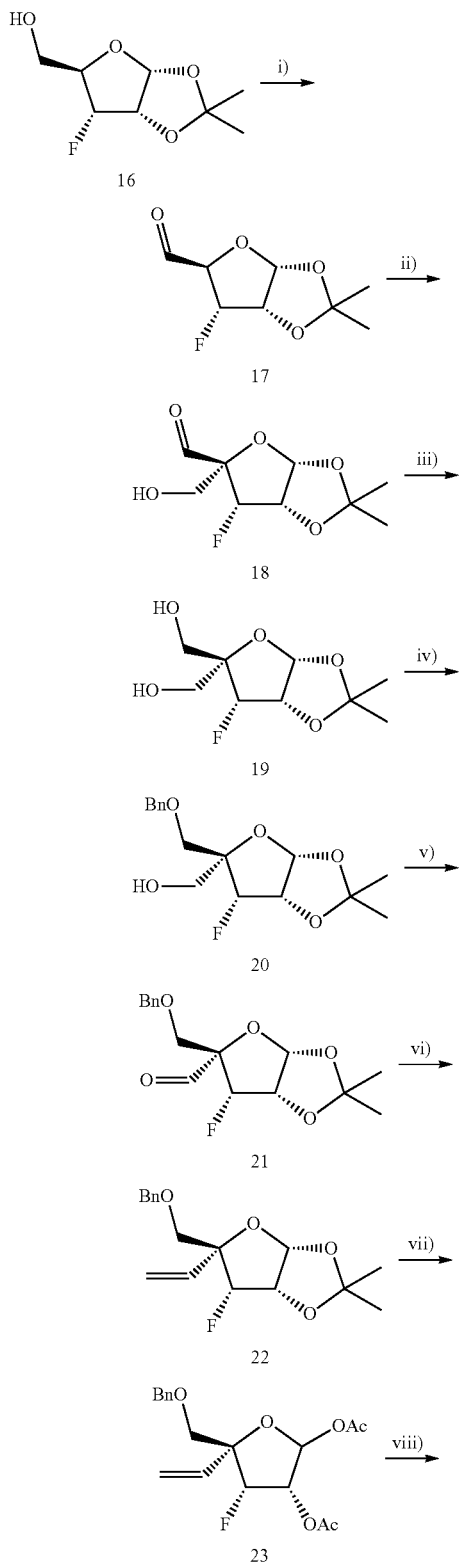

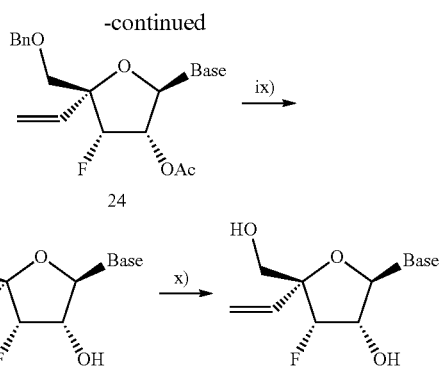

i) DMSO, (CO)$_2$Cl$_2$, CH$_2$Cl$_2$; ii) NaOH, CH$_2$O, Dioxane; iii) NaBH$_4$; iv) BnCl, NaH, DMF; v) Martin'S reagent, THF, CH$_2$Cl$_2$; vi) PPh$_3$CH$_3$I, BuLi, THF; vii) AcOH, Ac$_2$O, H$_2$SO$_4$; viii) Base, BSA, SnCl$_4$, MeCN; ix) NH$_3$·H$_2$O, Dioxane; x) BCl$_3$, Pyriine General Preparations Synthesis of Compound (3aR,5R,6S,6aR)-6-(benzyloxy)-5-(benzyloxymethyl)-2,2-dimethyl-5-vinyl-tetrahydrofuro[2,3-d][1,3]dioxole (2)

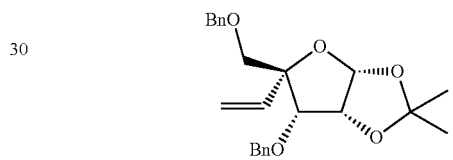

n-BuLi (3.7 mL, 2.5 mmol) was added into the solution of Ph$_3$PCH$_3$I (4.0 g, 10 mmol) in dry THF (25 mL) at 25° C., after addition, the reaction mixture was stirred at 40° C. for 2 hrs, then the solution was cooled to 0° C. and compound 1 (1.0 g, 2.5 mmol) was added into the mixture, removed the ice-bath, the reaction was stirred at 30° C. After 2 h, the reaction mixture was quenched by saturated aqueous NH$_4$Cl solution (10 mL), extracted with ether, washed with water, brine solution, dried (Na$_2$SO$_4$) and evaporated to dryness under reduced pressure.

Chromatography (petroleum ether:ethyl acetate 20:1 to 15:1) afforded 2 (0.72 g, 72%) as a colorless oil.

LC-MS: (M+Na)$^+$=419.2

$^1$H NMR (300 MHz, CDCl$_3$) δ 7.35-7.33 (m, 10H), 6.19 (dd, J=11.1 and 17.7 Hz, 1H), 5.76-5.75 (m, 1H), 5.51 (dd, J=1.8 and 17.7 Hz, 1H), 5.24 (dd, J=1.8 and 11.1 Hz, 1H), 4.76 (d, J=12.3 Hz, 1H), 4.60-4.24 (m, 4H), 1.51 (s, 4H), 1.28 (s, 6H).

Synthesis of Compound (3R,4S,5R)-4-(benzyloxy)-5-(benzyloxymethyl)-5-vinyl-tetra hydrofuran-2,3-diyl Diacetate (3)

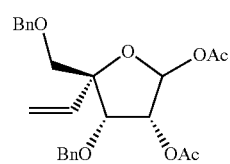

To a solution of 2 (0.72 g, 1.82 mmol) in AcOH/Ac$_2$O (16.5 mL/2 mL) was added H$_2$SO$_4$ (0.35 mL). After stirring at room temperature for 3 h, the reaction mixture was poured into ice-water and then treated with saturated aqueous NaHCO$_3$ (5 mL). The organic phase was extracted with ethyl acetate was washed with water, brine solution, dried (Na$_2$SO$_4$) and evaporated to dryness under reduced pressure. Chromatography column (Chromatography (petroleum ether:ethyl acetate 20:1 to 10:1) to afford the product 3 (0.471 g, 58%) as a white solid.

LC-MS: (M+Na)$^+$=463.1

$^1$H NMR (300 MHz, CDCl$_3$) δ 7.32-7.30 (m, 10H), 6.191 (s, 1H), 6.00-5.94 (m, 1H), 5.50 (dd, J=1.5 and 17.1 Hz, 1H), 5.31-5.23 (m, 2H), 4.66 (d, J=11.7 Hz, 1H), 4.51-4.42 (m, 4H), 3.42 (s, 2H), 2.06 (s, 3H), 1.87 (s, 3H).

Synthesis of Compound (2R,3R,4S,5R)-2-(4-amino-2-oxopyrimidin-1(2H)-yl)-4-(benzyloxy)-5-(benzyloxymethyl)-5-vinyl-tetrahydrofuran-3-yl Acetate (4)

BSA (0.976 g, 4.8 mmol) was added to a mixture of 4-aminopyrimidin-2(1H)-one (0.266 g, 2.4

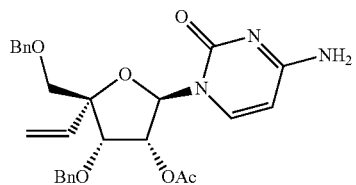

4 mmol) in CH$_3$CN (15 mL) at room temperature. After 3 h, 3 (0.53 g, 1.2 mmol) and SnCl$_4$ (1.35 g) were added into the mixture. Once complete, the mixture was stirred at 65° C. for 1 h, cooled and then poured into a saturated aqueous solution of NaHCO$_3$ (20 mL). The organic phase was extracted with ethyl acetate, washed with water, brine solution, dried (Na$_2$SO$_4$) and evaporated to dryness. Chromatography (dichloromethane:methanol 15:1) afforded 4 (0.564 g, 95%) as a brown solid.

LC-MS: (M+H)$^+$=492.2

Synthesis of Compound 4-amino-1-((2R,3R,4S,5R)-4-(benzyloxy)-5-(benzyloxymethyl)-3-hydroxy-5-vinyl-tetrahydrofuran-2-yl)pyrimidin-2(1H)-one (5)

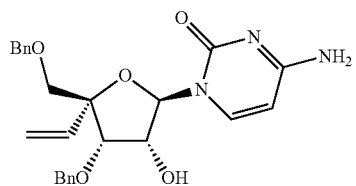

5

A solution of compound 4 (0.56 g, 1.14 mmol) in NH$_3$.MeOH (20 mL) was stirred at room temperature for 24 h and then evaporated to dryness under reduced pressure. Chromatography (dichloromethane:MeOH 15:1) provided 5 (0.5 g, 97%) as a white solid.

LC-MS: (M+H)$^+$=450.2

Synthesis of Compound 4-amino-1-((2R,3R,4S,5R)-3,4-dihydroxy-5-(hydroxymethyl)-5-vinyl-tetrahydrofuran-2-yl)pyrimidin-2(1H)-one (6)

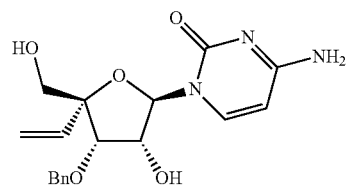

6

To a solution of compound 5 (0.112 g, 0.249 mmol) in dry dichloromethane (10 mL) was added BCl$_3$ (2.1 mL, 2.1 mmol) at −78° C. After stirring at −78° C. for 2 h, the reaction mixture was quenched by the addition of MeOH (1 mL), warmed to room temperature and evaporated to dryness under reduced pressure. Purification by prep-HPLC provided 6 (0.05 g, 74%) as a white solid.

LC-MS (M+H)$^+$=270.2

$^1$H NMR (300 MHz, DMSO-d$_6$) δ 7.84 (d, J=7.2 Hz, 1H), 7.17 (d, J=11.1 Hz, 1H), 5.93 (dd, J=10.5 and 17.1 Hz, 1H), 5.84 (d, J=5.4 Hz, 1H) 5.73 (d, J=7.5 Hz, 1H), 5.29-5.22 (m, 2H), 5.11-5.05 (m, 2H), 4.93-4.91 (d, J=5.1 Hz, 1H), 4.13-4.09 (m, 2H), 3.48-3.42 (m, 1H), 3.28 (d, J=11.7 Hz, 1H).

Synthesis of Compound (2R,3R,4S,5R)-4-(benzyloxy)-5-(benzyloxymethyl)-2-(2,4-dioxo-3,4-dihydropyrimidin-1(2H)-yl)-5-vinyl-tetrahydrofuran-3-yl Acetate (7)

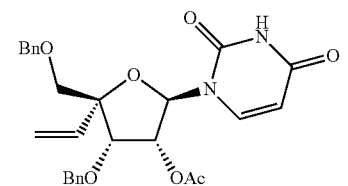

7

To a solution of pyrimidine-2,4(1H,3H)-dione (0.2 g, 1.8 mmol) in anhydrous CH$_3$CN was slowly added BSA (0.73 mL, 3.6 mmol), maintaining a reaction temperature below 25° C. Once the reaction mixture solubilized, compound 6 (0.4 g, 0.9 mmol) in CH$_3$CN (5 mL) was added at 0° C. followed by SnCl$_4$ (1.17 g, 3.6 mmol). The mixture was stirred at 65° C. for 1 h and then poured into saturated NaHCO$_3$ (5 mL) at 0° C. The organic phase was extracted with ethyl acetate, washed with water, brine solution, dried (Na$_2$SO$_4$) and evaporated to dryness under reduced pressure. Chromatography (Petroleum ether:thyl acetate 1:1) gave 7 as an colorless oil (0.4 g, 90%).

LC-MS: (M+H)$^+$=493;

Synthesis of Compound 1-((2R,3R,4S,5R)-4-(benzyloxy)-5-(benzyloxymethyl)-3-hydroxy-5-vinyl-tetrahydrofuran-2-yl)pyrimidine-2,4(1H,3H)-dione (8)

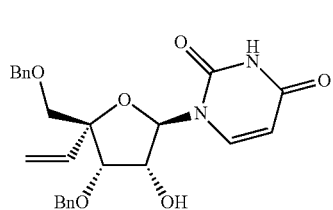

A mixture of compound 7 (0.4 g, 0.81 mmol) in NH$_3$.MeOH (16 mL) was stirred at 25° C. for 16 h and then evaporated to dryness under reduced pressure. Chromatography (dichloromethane:methanol; 20:1) provided 8 as an colorless oil (0.285 g, 78%).

LC-MS (M+H)$^+$=451;

Synthesis of Compound 1-((2R,3R,4S,5R)-3,4-dihydroxy-5-(hydroxymethyl)-5-vinyl-tetrahydrofuran-2-yl)pyrimidine-2,4(1H,3H)-dione (9)

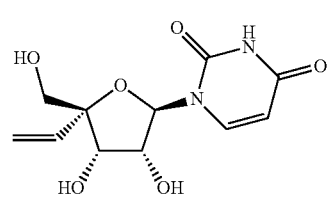

To a solution of compound 8 (0.36 g, 0.8 mmol) in dry dichloromethane (20 mL), cooled to −78° C., was added BCl$_3$ (6 mL, 6 mmol). After stirring at −78° C. for 2 h, the reaction mixture was quenched by MeOH (0.5 mL), warmed to room temperature and evaporated to dryness under reduced pressure. Purification by prep-HPLC provided 9 (0.06 g, 25%) as a white solid.

LC-MS (M+H)$^+$=271.1
$^1$H NMR (300 MHz, d$_6$-DMSO) δ 11.317 (brs, 1H), 7.93 (d, J=8.1 Hz, 1H), 5.97-5.84 (m, 2H), 5.68 (d, J=8.1 Hz, 1H), 5.29-5.02 (m, 5H), 4.17-4.10 (m, 2H), 3.50-3.46 (m, 1H), 3.34-3.27 (m, 1H).

Synthesis of Compound (10)

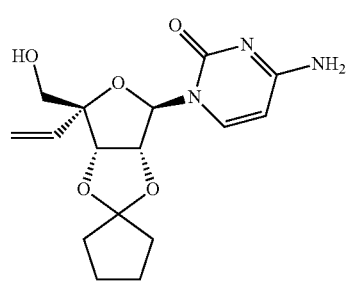

To a mixture of compound 6 (0.08 g, 0.3 mmol) and 1,1-dimethoxycyclopentane (0.387 g, 3 mmol) in anhydrous 1,2-dichloroethane was added p-toluenesulfonic acid (0.04 g, 0.24 mmol). The resulting mixture was stirred at 65° C. for 1 h, cooled to room temperature and evaporated to dryness under reduced pressure. Chromatography (dichloromethane:methanol 5:1) gave 10 as a white solid (0.08 g, 82%).

LC-MS (M+H)$^+$=270.1

Synthesis of (S)-1-(benzyloxy)-1-oxopropan-2-aminium Chloride (27)

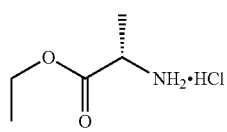

To a solution of (S)-alanine (5.0 g, 56 mmol) in dry EtOH (100 mL) was added SOCl$_2$ (8.0 g, 60 mmol) dropwise at −20° C. over 20 min. Once complete, the resulting mixture was stirred at 78° C. for 5 h, cooled and then evaporated to dryness under reduced pressure. The residue was triturated with Et$_2$O, filtered and dried under vacuum to give the crude product 27, which was used directly without further purification (8.0 g, 90%).

LC-MS (M)$^+$=118.2

Synthesis of (2S)-benzyl 2-(chloro(phenoxy)phosphorylamino)propanoate (28)

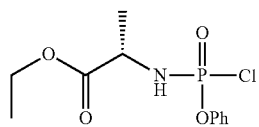

To a solution of 27 (5.0 g, 33 mmol) and Et$_3$N (3.6 g, 36 mmol) in dry dichloromethane (100 mL), at −78° C. under a nitrogen atmosphere, was added phenyl phosphorodichloridate (6.85 g, 33 mmol). The resulting mixture was stirred at −78° C. for 1 h and then warmed to room temperature. After stirring for further 5 h, the reaction mixture was evaporated to dryness under reduced pressure. Chromatography (petroleum ether:ethyl acetate 5:1) gave 28 as an colorless oil (9.0 g, 95%).

LC-MS (M+H)$^+$=292.1

Synthesis of Compound (29)

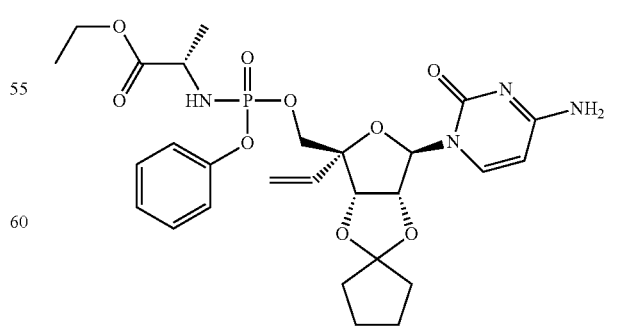

To a suspension of compound 10 (0.08 g, 0.23 mmol) in anhydrous THF, cooled to 0° C. and under nitrogen atmosphere, was added t-BuMgBr (1.84 mL, 1.84 mmol). The resulting mixture was allowed to warm to room temperature and stirred for 30 min. The reaction mixture was then cooled to 0° C. and (2S)-ethyl 2-(chloro(phenoxy)phosphorylamino)propanoate 28 (0.267 g, 0.92 mmol) was added drop-wise over 10 min. The resulting mixture was stirred at room temperature for 2 h and then quenched with 1 mL MeOH followed by evaporation to dryness under reduced pressure. Chromatography (dichloromethane:methanol 20:1 to 15:1) afforded 29 as a white solid (0.14 g, crude).

LC-MS (M+H)$^+$=591.2

Synthesis of Compound (S)-benzyl 2-((((2R,3S,4R,5R)-5-(4-amino-2-oxopyrimidin-1(2H)-yl)-2-(difluoromethyl)-3,4-dihydroxy-tetrahydrofuran-2-yl)methoxy)(phenoxy)phosphorylamino)propanoate (30)

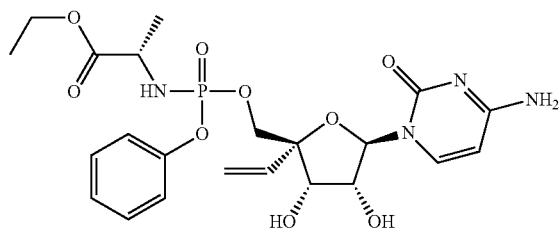

30

A solution of compound 29 (0.14 g, 0.26 mmol) in HCO$_2$H (80%, v/v; 10 mL) was stirred at 25° C. for 18 h and then evaporated to dryness under reduced pressure. Purification by pre-HPLC provided 30 as a white solid (28 mg, 22%).

LC-MS (M+H)$^+$=525.2

$^1$H NMR (300 MHz, DMSO-d$_6$) δ 7.58 (m, 1H), 7.39 (m, 2H), 7.21 (m, 5H), 6.10-5.91 (m, 3H), 5.69 (m, 1H), 5.37-5.19 (m, 4H), 4.13-3.90 (m, 7H), 1.25-1.16 (m, 6H).

Synthesis of Compound (31)

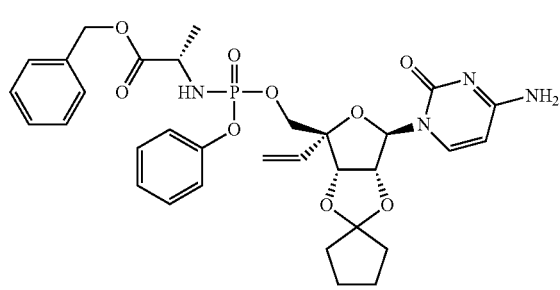

31 t-BuMgBr (1.6 mL, 1.6 mmol) was added to a cooled (0° C.) suspension of compound 10 (0.09 g, 0.27 mmol) in dry THF (36 mL). The reaction mixture was left to stir under a nitrogen atmosphere for 30 min. (2S)-Benzyl 2-(chloro(phenoxy)phosphorylamino)propanoate (0.285 g, 0.807 mmol) was added drop-wise at 0° C. over 10 min. Once complete, the reaction mixture was stirred for 16 h at room temperature and then quenched with 1 mL MeOH. The resulting mixture was evaporated to dryness under reduced pressure. Chromatography (dichloromethane:methanol 20:1 to 10:1) afforded 31 as a white solid (0.15 g, crude).

LC-MS (M+H)$^+$=653.2

Synthesis of Compound (S)-benzyl 2-((((2R,3S,4R,5R)-5-(4-amino-2-oxopyrimidin-1(2H)-yl)-2-(difluoromethyl)-3,4-dihydroxy-tetrahydrofuran-2-yl)methoxy)(phenoxy)phosphorylamino)propanoate (32)

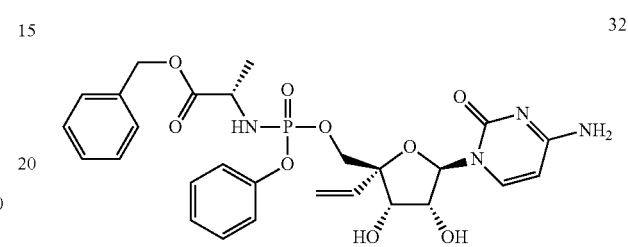

32

A solution of compound 31 (0.15 g, 0.23 mmol) in HCO$_2$H (80%, v/v, 30 mL) was stirred at room temperature for 18 h and then evaporated to dryness under reduced pressure. The residue was treated with saturated aqueous NaHCO$_3$ solution until pH=7 persisted. The organic phase was extracted with ethyl acetate, washed water, brine solution, dried (Na$_2$SO$_4$) and evaporated to dryness under reduced pressure. Purification by prep-HPLC provided 32 as a white solid (17 mg, 9%).

LC-MS (M+H)$^+$=587.2

$^1$H NMR (300 MHz, DMSO-d$_6$) δ 7.56 (m, 1H), 7.34 (m, 7H), 7.34-7.17 (m, 5H), 6.19-6.15 (m, 1H), 6.12-5.90 (m, 2H), 5.72-5.66 (dd, 1H), 5.35 (m, 1H), 5.20-5.09 (m, 5H), 4.15-3.89 (m, 5H), 1.25 (t, J=7.5 Hz, 3H).

Synthesis of Compound (2R,3R,4S,5R)-2-(6-amino-9H-purin-9-yl)-4-(benzyloxy)-5-(benzyloxymethyl)-5-vinyl-tetrahydrofuran-3-yl Acetate (33)

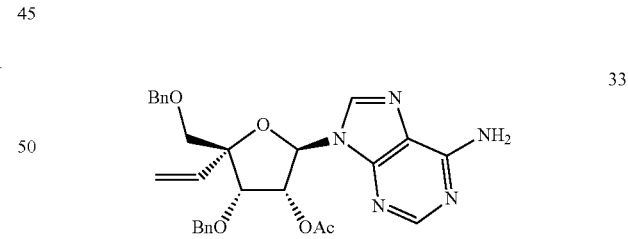

33

To a solution of compound 9H-purin-6-amine (0.307 g, 2.28 mmol) and 3 (0.5 g, 1.14 mmol) in anhydrous CH$_3$CN was added SnCl$_4$ (0.57 mL, 4.9 mmol) portion-wise while maintaining the reaction temperature at 25° C. Once complete, the reaction mixture was stirred for 16 h and then poured into saturated aqueous solution of NaHCO$_3$ at 0° C. The organic phase was extracted with ethyl acetate, washed with water, brine solution, dried (Na$_2$SO$_4$) and evaporated to dryness under reduced pressure. Chromatography (petroleum ether:ethyl acetate 1:1) provided 33 as a white solid (0.395 g, 67%).

LC-MS: (M+H)$^+$=516

Synthesis of Compound (2R,3R,4S,5R)-2-(6-amino-9H-purin-9-yl)-4-(benzyloxy)-5-(benzyloxymethyl)-5-vinyl-tetrahydrofuran-3-ol (34)

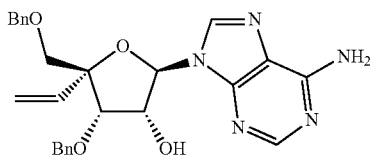

34

A mixture of compound 33 (0.395 g, 0.77 mmol) in NH$_3$-MeOH/dioxane (15 mL/15 mL) was stirred at 25° C. for 16 h and then evaporated to dryness under reduced pressure. Chromatography (petroleum ether:ethyl acetate 1:1) afforded 34 as a white solid (0.324 g, 96%).
LC-MS (M+H)$^+$=474

Synthesis of Compound (2R,3S,4R,5R)-5-(6-amino-9H-purin-9-yl)-2-(hydroxymethyl)-2-vinyl-tetrahydrofuran-3,4-diol (35)

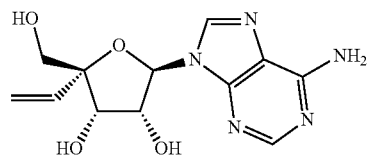

35

To a solution of compound 34 (0.304 g, 0.64 mmol) in anhydrous dichloromethane (20 mL), at −78° C. and under a nitrogen atmosphere, was added BCl$_3$ (5.4 mL, 5.4 mmol). After stirring at −78° C. for 4 h, the reaction mixture was quenched by the addition of MeOH. The resulting mixture was allowed to warm to room temperature and then evaporated to dryness under reduced pressure. Purification by prep-HPLC provided 35 (0.058 g, 29%) as a white solid.
LC-MS (M+H)$^+$=294.1
$^1$H NMR (300 MHz, d$_6$-DMSO) δ 8.35 (s, 1H), 8.14 (s, 1H), 7.39 (s, 2H), 6.02-5.85 (m, 3H), 5.33-5.26 (m, 2H), 5.15-5.10 (m, 2H), 4.81-4.79 (m, 1H), 4.23 (t, J=4.8 Hz, 1H), 3.48-3.44 (m, 2H).

Synthesis of Compound (2R,3R,4S,5R)-4-(benzyloxy)-5-(benzyloxymethyl)-2-(2-isobutyramido-6-oxo-1,6-dihydropurin-9-yl)-5-vinyl-tetrahydrofuran-3-yl Acetate (36)

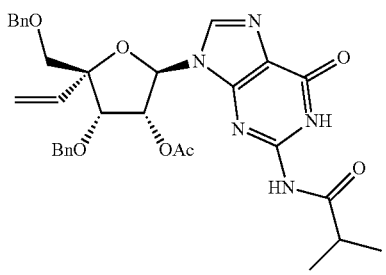

36

Compound 3 (1 g, 2.27 mmol) was added to a mixture of BSA (1.38 g, 6.81 mmol) and N-(6-oxo-6,9-dihydro-1H-purin-2-yl)isobutyramide (0.752 g, 3.4 mmol) in CH$_3$CN (15 mL), under nitrogen atmosphere, in one portion. Once complete, the mixture was stirred for 3 h. To the resulting clear solution was added TMSOTf (1.51 g, 6.81 mmol). The reaction mixture was stirred at 60° C. for 16 h, cooled to 0° C. and then poured onto saturated aqueous solution of NaHCO$_3$. The organic phase was extracted with ethyl acetate, washed with water, brine solution, dried (Na$_2$SO$_4$) and evaporated to dryness. Chromatography (petroleum ether:ethyl acetate 1:1) provided 36 (0.7 g, 51%) as a white solid.

Synthesis of Compound 2-amino-9-((2R,3R,4S,5R)-4-(benzyloxy)-5-(benzyloxy methyl)-3-hydroxy-5-vinyl-tetrahydrofuran-2-yl)-1H-purin-6(9H)-one (37)

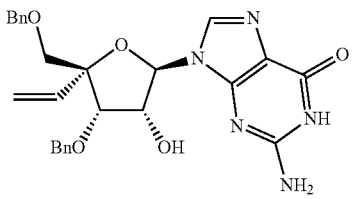

37

A solution of compound 36 (0.65 g, 1.08 mmol) in NH$_3$-MeOH (10 mL) was stirred at room temperature for 48 h and then evaporated to dryness under reduced pressure to give 37 (0.5 g, crude) as a white solid, which was used directly without further purification.

Synthesis of Compound 2-amino-9-((2R,3R,4S,5R)-3,4-dihydroxy-5-(hydroxymethyl)-5-vinyl-tetrahydrofuran-2-yl)-1H-purin-6(9H)-one (38)

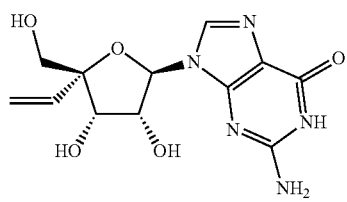

38

To a solution of 37 (0.5 g, 1.02 mmol) in anhydrous dichloromethane (10 mL) was added BCl$_3$ (10 mL, 10.2 mmol) at −50° C. under a nitrogen atmosphere. Once complete, the reaction was stirred at −20° C. for 3 h and then quenched by the addition of MeOH (6 mL), warmed to room temperature and then evaporated to dryness under reduced pressure. Purification by prep-HPLC afforded 38 (0.054 g, 17%) as a white solid.
LC-MS (M+H)$^+$=310.1
$^1$H NMR (300 MHz, DMSO-d$_6$) δ 10.59 (s, 1H), 7.98 (s, 1H), 6.46 (s, 2H), 6.03-5.94 (q, 1H), 5.75-5.73 (d, 1H), 5.33-5.26 (m, 3H), 5.15-5.11 (dd, 1H), 5.05-5.04 (d, 1H), 4.62-4.56 (q, 1H), 4.24-4.20 (t, 1H), 3.50-3.36 (m, 2H).

Biological Examples

TABLE 2

Activity of nucleoside triphosphate analogs as inhibitors of RNA synthesis by RSV polymerase.

| Compound Number | Structure | IC$_{50}$ [a] |
|---|---|---|
| II-1 | (triphosphate-sugar-uracil with vinyl, HO, OH) | A |
| II-2 | (triphosphate-sugar-cytosine with vinyl, HO, OH) | A |
| II-3 | (triphosphate-sugar-adenine with vinyl, HO, OH) | A |
| II-4 | (triphosphate-sugar-guanine with vinyl, HO, OH) | A |
| II-5 | (triphosphate-sugar-uracil with vinyl, F, OH) | |
| II-6 | (triphosphate-sugar-cytosine with vinyl, F, OH) | |

[a] RSV polymerase inhibition with A = IC$_{50}$ < 1 μM

RSV Assays

The RSV polymerase assay measures the ability of the nucleoside triphosphates derived from compounds of formula I to inhibit the RSV polymerase. RSV polymerase was obtained from RSV infected A549 cells. RSV polymerase activity was measured using RSV polymerase preparation (stored in 10 mM Tris-acetate (pH 8), 10 mM K-acetate, 1.5 mM MgCl$_2$, 0.5% deoxycholate and 1% Tween-40) in the a buffer containing 50 mM Tris-HCL, pH8, 100 mM KCl, 5 mM MgCl$_2$, 1 mM DTT and 0.2 mg/ml BSA in the presence of 50 μM ATP, GTP and UTP, 1 μM CTP and 3.5 μCi $^{33}$P-labeled CTP (10 mCi/mL). The amount of nucleotides incorporated into nascent RSV RNA was determined TCA precipitation and scintillation counting.

RSV replication was measured in cell culture in RSV infected Hep-2 or Huh-7 cells. Cell culture supernatant containing RSV particles was collected and the RSV virus concentration was determined using ELISA, RT-PCR and plaque assays.

The polymerase and replication activities of RSV were measured in the presence and absence of different concentrations of compounds to determine the degree of inhibition by the compounds.

The compound concentration at which the enzyme-catalyzed rate is reduced by 50% ($IC_{50}$) was calculated by fitting the data to equation (1), $$Y = \% \text{ Min} + \frac{(\% \text{ Max} - \% \text{ Min})}{\left(1 + \frac{X}{(IC_{50})^S}\right)} \quad (1)$$

where "Y" corresponds to the relative enzyme activity (in %), "% Min" is the residual relative activity at saturating compound concentration, "% Max" is the relative maximum enzymatic activity, X corresponds to the compound concentration, and "S" is the Hill coefficient (or slope).

Dosage and Administration:

As shown in above Table the compounds of formula I have the potential to be efficacious as antiviral drugs for the treatment of RSV infections in humans, or are metabolized to a compound that exhibit such activity.

In another embodiment of the invention, the active compound or its prodrug derivative or salt can be administered in combination with another antiviral agent, such as an anti-hepatitis agent, including those of formula I. When the active compound or its derivative or salt are administered in combination with another antiviral agent the activity may be increased over the parent compound. This can easily be assessed by preparing the derivative and testing its anti-RSV activity according to the method described herein.

Administration of the active compound may range from continuous (intravenous drip) to several oral administrations per day (for example, Q.I.D) and may include oral, topical parenteral, intramuscular, intravenous, subcutaneous, transdermal (which may include a penetration enhancement agent), buccal and suppository administration, among other routes of administration.

The 4'-vinyl substituted nucleoside derivatives as well as their pharmaceutically useable salts, can be used as medicaments in the form of any pharmaceutical formulation. The pharmaceutical formulation can be administered enterally, either orally, e.g. in the form of tablets, coated tablets, dragées, hard and soft gelatine capsules, solutions, emulsions, syrups, or suspensions, or rectally, e.g. in the form of suppositories. They can also be administered parenterally (intramuscularly, intravenously, subcutaneously or intrasternal injection or infusion techniques), e.g. in the form of injection solutions, nasally, e.g. in the form of nasal sprays, or inhalation spray, topically and so forth.

For the manufacture of pharmaceutical preparations, the 4'-substituted nucleoside derivatives, as well as their pharmaceutically useable salts, can be formulated with a therapeutically inert, inorganic or organic excipient for the production of tablets, coated tablets, dragées, hard and soft gelatine capsules, solutions, emulsions or suspensions.

The compounds of formula I can be formulated in admixture with a pharmaceutically acceptable carrier. For example, the compounds of the present invention can be administered orally as pharmacologically acceptable salts. Because the compounds of the present invention are mostly water soluble, they can be administered intravenously in physiological saline solution (e.g., buffered to a pH of about 7.2 to 7.5). Conventional buffers such as phosphates, bicarbonates or citrates can be used for this purpose. Of course, one of ordinary skill in the art may modify the formulations within the teachings of the specification to provide numerous formulations for a particular route of administration without rendering the compositions of the present invention unstable or compromising their therapeutic activity. In particular, the modification of the present compounds to render them more soluble in water or other vehicle, for example, may be easily accomplished by minor modifications (salt formulation, esterification, etc.) which are well within the ordinary skill in the art. It is also well within the ordinary skill of the art to modify the route of administration and dosage regimen of a particular compound in order to manage the pharmacokinetics of the present compounds for maximum beneficial effect in patients.

For parenteral formulations, the carrier will usually comprise sterile water or aqueous sodium chloride solution, though other ingredients including those which aid dispersion may be included. Of course, where sterile water is to be used and maintained as sterile, the compositions and carriers must also be sterilized. Injectable suspensions may also be prepared, in which case appropriate liquid carriers, suspending agents and the like may be employed.

Suitable excipients for tablets, coated tablets, dragées, and hard gelatin capsules are, for example, lactose, corn starch and derivatives thereof, talc, and stearic acid or its salts.

If desired, the tablets or capsules may be enteric-coated or sustained release by standard techniques.

Suitable excipients for soft gelatine capsules are, for example, vegetable oils, waxes, fats, semi-solid and liquid polyols.

Suitable excipients for injection solutions are, for example, water, saline, alcohols, polyols, glycerin or vegetable oils.

Suitable excipients for suppositories are, for example, natural and hardened oils, waxes, fats, semi-liquid or liquid polyols.

Suitable excipients for solutions and syrups for enteral use are, for example, water, polyols, saccharose, invert sugar and glucose.

The pharmaceutical preparations of the present invention may also be provided as sustained release formulations or other appropriate formulations.

The pharmaceutical preparations can also contain preservatives, solubilizers, stabilizers, wetting agents, emulsifiers, sweeteners, colorants, flavourants, salts for adjustment of the osmotic pressure, buffers, masking agents or antioxidants.

The pharmaceutical preparations may also contain other therapeutically active agents known in the art.

The dosage can vary within wide limits and will, of course, be adjusted to the individual requirements in each particular case. For oral administration, a daily dosage of between about 0.01 and about 100 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 100 mg/kg body weight per day. A typical preparation will contain from about 5% to about 95% active compound (w/w). The daily dosage can be administered as a single dosage or in divided dosages, typically between 1 and 5 dosages per day.

In certain pharmaceutical dosage forms, the pro-drug form of the compounds, especially including acylated (acetylated or other) derivatives, pyridine esters and various salt forms of the present compounds are preferred. One of ordinary skill in the art will recognize how to readily modify the present compounds to pro-drug forms to facilitate delivery of active compounds to a target site within the host organism or patient. One of ordinary skill in the art will also take advantage of favorable pharmacokinetic parameters of the pro-drug forms, where applicable, in delivering the present compounds to targeted site within the host organism or patient to maximize the intended effect of the compound.

Indications and Method of Treatment

The application provides a method for treating an RSV infection comprising administering to a patient in need thereof a therapeutically effective amount of a compound of Formula I.

The application provides the above method, further comprising administering an immune system modulator or one or more antiviral agents that inhibits replication of RSV, or a combination thereof.

The application provides the above method for inhibiting replication of RSV in a cell comprising administering a compound of Formula I.

Combination Therapy

The compounds of the invention and their isomeric forms and pharmaceutically acceptable salts thereof are useful in treating and preventing RSV infection alone or when used in combination with other compounds targeting viral or cellular elements or functions involved in the RSV lifecycle or immunomodulators. Classes of compounds useful in the invention include, without limitation, all classes of RSV antivirals.

Additionally, combinations of, for example, with an interferon, may be administered as multiple combination therapy with at least one of the compounds of the invention. The present invention is not limited to the aforementioned classes or compounds and contemplates known and new compounds and combinations of biologically active agents. It is intended that combination therapies of the present invention include any chemically compatible combination of a compound of this inventive group with other compounds of the inventive group or other compounds outside of the inventive group, as long as the combination does not eliminate the anti-viral activity of the compound of this inventive group or the anti-viral activity of the pharmaceutical composition itself.

Combination therapy can be sequential, that is treatment with one agent first and then a second agent (for example, where each treatment comprises a different compound of the invention or where one treatment comprises a compound of the invention and the other comprises one or more biologically active agents) or it can be treatment with both agents at the same time (concurrently). Sequential therapy can include a reasonable time after the completion of the first therapy before beginning the second therapy. Treatment with both agents at the same time can be in the same daily dose or in separate doses. Combination therapy need not be limited to two agents and may include three or more agents. The dosages for both concurrent and sequential combination therapy will depend on absorption, distribution, metabolism and excretion rates of the components of the combination therapy as well as other factors known to one of skill in the art. Dosage values will also vary with the severity of the condition to be alleviated. It is to be further understood that for any particular subject, specific dosage regimens and schedules may be adjusted over time according to the individual's need and the judgment of the one skilled in the art administering or supervising the administration of the combination therapy.

The application provides a method for treating an RSV infection comprising administering to a patient in need thereof a therapeutically effective amount of a compound of any one of Formula I.

The application provides the above method, further comprising administering an immune system modulator or an antiviral agent that inhibits replication of RSV, or a combination thereof.

The application provides the above method, wherein the immune system modulator is an interferon or chemically derivatized interferon.

It will be understood that references herein to treatment extend to prophylaxis as well as to the treatment of existing conditions, and that the treatment of animals includes the treatment of humans as well as other mammals. Furthermore, treatment of an RSV infection, as used herein, also includes treatment or prophylaxis of a disease or a condition associated with or mediated by an RSV infection, or the clinical symptoms thereof.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:

1. A compound of formula I,

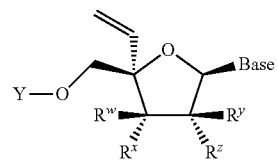

wherein:
Y is P(=X)(R)(R');
R is O—$R^1$ or NHC($R^{2a}$)($R^{2b}$)C(=O)O$R^3$;
R' is N($R^4$)C($R^{2a}$)($R^{2b}$)C(=O)O$R^3$, OP(=O)(OH)OP(=O)(OH)OH, or O$R^3$;
$R^1$ is naphthyl, optionally substituted with one or more lower alkyl, lower alkenyl, lower alkynyl, lower alkoxy, halo, lower haloalkyl, —N($R^{1a}$)$_2$, acylamino, —SO$_2$N($R^{1a}$)$_2$, —C(=O)$R^{1b}$, —SO$_2$$R^{1c}$, —NHSO$_2$$R^{1c}$, nitro, cyano, or $R^{1''}$;
each $R^{1a}$ is independently H or lower alkyl;
each $R^{1b}$ is independently —O$R^{1a}$ or —N($R^{1a}$)$_2$;
each $R^{1c}$ is lower alkyl;

each $R^{2a}$ and $R^{2b}$ is independently H, lower alkyl, —(CH$_2$)$_r$N(R$^{1a}$)$_2$, lower hydroxyalkyl, —CH$_2$SH, —(CH$_2$)S(O)$_p$Me, —(CH$_2$)$_n$NHC(=NH)NH$_2$, (1H-indol-3-yl)Me, (1H-indol-4-yl)Me, —(CH$_2$)$_m$C(=O)R$^{1b}$, aryl or aryl lower alkyl, wherein aryl and aryl lower alkyl are optionally substituted with one or more hydroxy, lower alkyl, lower alkoxy, halo, nitro or cyano;
  m is 0, 1, or 2;
  n is 1, 2, or 3;
  p is 1 or 2;
  r is 1 or 2;
or $R^{2a}$ is H and $R^{2b}$ and $R^4$ together form (CH$_2$)$_n$;
each $R^3$ is independently H, lower alkyl, lower haloalkyl, or phenyl lower alkyl, wherein phenyl lower alkyl is optionally substituted with lower alkoxy;
or $R^3$ and $R^{1'''}$ together form CH$_2$;
each $R^4$ is independently H, lower alkyl;
or $R^{2b}$ and $R^4$ together form (CH$_2$)$_3$;
both of $R^w$ and $R^y$ are H;
$R^x$ is F or OH;
$R^z$ is OH;
or $R^3$ and $R^x$ together form a bond;
or $R^1$ and $R^x$ together form a bond;
X is O or S; and
Base is uracil, cytosine, guanine, adenine, thymine, or heterocycloalkyl, each of which may optionally be substituted with one or more hydroxy, lower alkyl, lower alkoxy, halo, nitro or cyano;
or a pharmacologically acceptable salt thereof.

2. The compound of claim 1, wherein R' is O—R$^3$, R$^3$ is lower alkyl, R is —OR$^1$, and R$^1$ and R$^x$ together form a bond.

3. The compound of claim 1, wherein R is —OR$^1$, R$^1$ is naphthyl substituted with R$^{1'''}$, R' is —OR$^3$, and R$^3$ and R$^{1'''}$ together form CH$_2$.

4. The compound of claim 1, wherein X is O.

5. The compound of claim 1, wherein X is S.

6. The compound of claim 1, wherein R is O—R$^1$, and R$^1$ is naphthyl.

7. The compound of claim 1, wherein R' is N(R$^4$)C(R$^{2a}$)(R$^{2b}$)C(=O)OR$^3$, R$^4$ is H, R$^{2a}$ is H, R$^{2b}$ is methyl, and R$^3$ is isopropyl.

8. The compound of claim 1, wherein R' is —OP(=O)(OH)OP(=O)(OH)OH.

9. The compound of claim 1, wherein Base is cytidine optionally substituted with halo.

10. The compound of claim 1, wherein Base is uridine optionally substituted with halo.

11. The compound of claim 1, wherein $R^x$ is F.

12. A compound selected from the list consisting of:
4'-Vinyluridine-5'-(O-1-naphthyl-N—(S)-1-(isopropoxycarbonyl)ethyl phosphoramidate;
4'-Vinyluridine-5'-(O-1-naphthyl-N—(S)-1-(i2,2-dimethylpropoxycarbonyl)ethyl phosphoramidate;
4'-Vinyluridine-5'-(O-1-naphthyl-N—(S)-1-(3,3-dimethylbutoxycarbonyl)ethyl phosphoramidate;
4'-Vinyluridine-5'-(O-1-naphthyl-N—(S)-1-(benzyloxycarbonyl)ethyl phosphoramidate;
4'-Vinyluridine-5'-(O-1-naphthyl-N—(S)-1-(hexoxycarbonyl)ethyl phosphoramidate;
4'-Vinyluridine-5'-(O-1-naphthyl-N—(S)-1-(cyclopentoxycarbonyl)ethyl phosphoramidate;
4'-Vinyluridine-5'-(O-1-naphthyl-N—(S)-1-(cyclohexoxycarbonyl)ethyl phosphoramidate;
4'-Vinyluridine-5'-(O-2-naphthyl-N—(S)-1-(isopropoxycarbonyl)ethyl phosphoramidate;
4'-Vinyluridine-5'-{N,N'-bis[(S)-1-(isopropoxycarbonyl)ethyl]phosphorodiamidate};
4'-Vinyluridine-5'-{N,N'-bis[(S)-1-(2,2-dimethylpropoxycarbonyl)ethyl]phosphorodiamidate};
4'-Vinyluridine-5'-{N,N'-bis[(S)-1-(3,3-dimethylbutoxycarbonyl)ethyl]phosphorodiamidate};
4'-Vinyluridine-5'-{N,N'-bis[(S)-1-(benzyloxycarbonyl)ethyl]phosphorodiamidate};
4'-Vinyluridine-5'-{N,N'-bis[(S)-1-(hexoxycarbonyl)ethyl]phosphorodiamidate};
4'-Vinyluridine-5'-{N,N'-bis[(S)-1-(cyclopentoxycarbonyl)ethyl]phosphorodiamidate};
4'-Vinyluridine-5'-{N,N'-bis[(S)-1-(cyclohexoxycarbonyl)ethyl]phosphorodiamidate};
4'-Vinyl-5'-O-(2-oxido-4-H-1,3,2-benzodioxaphosphorin-2-yl)-uridine;
4'-Vinyl-5'-O-[bis(4-methoxyphenoxy)phosphinyl] uridine;
4'-Vinyluridine-3',5'-cyclic phosphoric acid isopropyl ester;
4'-Vinylcytidine-5'-(O-1-naphthyl-N—(S)-1-(isopropoxycarbonyl)ethyl phosphoramidate;
4'-Vinylcytidine-5'-(O-1-naphthyl-N—(S)-1-(2,2-dimethylpropoxycarbonyl)ethyl phosphoramidate;
4'-Vinylcytidine-5'-(O-1-naphthyl-N—(S)-1-(benzyloxycarbonyl)ethyl phosphoramidate;
4'-Vinylcytidine-5'-(O-1-naphthyl-N—(S)-1-(3,3-dimethybutoxycarbonyl)ethyl phosphoramidate;
4'-Vinyl cytidine-5'-(O-1-naphthyl-N—(S)-1-(pentoxycarbonyl)ethyl phosphoramidate;
4'-Vinyl cytidine-5'-(O-1-naphthyl-N—(S)-1-(hexoxycarbonyl)ethyl phosphoramidate;
4'-Vinyl cytidine-5'-(O-1-naphthyl-N—(S)-1-(cyclohexoxycarbonyl)ethyl phosphoramidate;
4'-Vinylcytidine-5'-(O-2-naphthyl-N—(S)-1-(isopropoxycarbonyl)ethyl phosphoramidate;
4'-Vinylcytidine-5'-{N,N'-bis[(S)-1-(isopropoxycarbonyl)ethyl]phosphorodiamidate};
4'-Vinylcytidine-5'-{N,N'-bis[(S)-1-(2,2-dimethylpropoxycarbonyl)ethyl]phosphorodiamidate};
4'-Vinylcytidine-5'-{N,N'-bis[(S)-1-benzyloxycarbonyl)ethyl]phosphorodiamidate};
4'-Vinylcytidine-5'-{N,N'-bis[(S)-1-(3,3-dimethylbutoxycarbonyl)ethyl]phosphorodiamidate};
4'-Vinylcytidine-5'-{N,N'-bis[(S)-1-(hexoxycarbonyl)ethyl]phosphorodiamidate};
4'-Vinylcytidine-5'-{N,N'-bis[(S)-1-(cyclohexoxycarbonyl)ethyl]phosphorodiamidate};
4'-Vinyl-5'-O-(2-oxido-4-H-1,3,2-benzodioxaphosphorin-2-yl)-cytidine;
4'-Vinyl-5'-O-[bis(4-methoxyphenoxy)phosphinyl] cytidine;
4'-Vinylcytidine-3',5'-cyclic phosphoric acid isopropyl ester;
4'-Vinyl adenosine-5'-(O-1-naphthyl-N—(S)-1-(isopropoxycarbonyl)ethyl phosphoramidate;
4'-Vinyladenosine-5'-(O-2-naphthyl-N—(S)-1-(isopropoxycarbonyl)ethyl phosphoramidate;
4'-Vinyladenosine-5'-{N,N'-bis[(S)-1-(isopropoxycarbonyl)ethyl]phosphorodiamidate};
4'-Vinyl-5'-O-(2-oxido-4-H-1,3,2-benzodioxaphosphorin-2-yl)-adenosine;
4'-Vinyl-5'-O-[bis(4-methoxyphenoxy)phosphinyl] adenosine;

4'-Vinyladenosine-3',5'-cyclic phosphoric acid isopropyl ester;
4'-Vinylguanosine-5'-(O-1-naphthyl-N—(S)-1-(isopropoxycarbonyl)ethyl phosphoramidate;
4'-Vinylguanosine-5'-(O-2-naphthyl-N—(S)-1-(isopropoxycarbonyl)ethyl phosphoramidate;
4'-Vinylguanosine-5'-{N,N'-bis[(S)-1-(isopropoxycarbonyl)ethyl]phosphorodiamidate};
4'-Vinyl-5'-O-(2-oxido-4-H-1,3,2-benzodioxaphosphorin-2-yl)-guanosine;
4'-Vinyl-5'-O-[bis(4-methoxyphenoxy)phosphinyl] guanosine;
4'-Vinylguanosine-3',5'-cyclic phosphoric acid isopropyl ester;
3'-Deoxy-3'-fluoro-4'-vinyluridine-5'-(O-1-naphthyl-N—(S)-1-(isopropoxycarbonyl)ethyl phosphoramidate;
3'-Deoxy-3'-fluoro-4'-vinyluridine-5'-(O-1-naphthyl-N—(S)-1-(2,2-dimethylpropoxycarbonyl)ethyl phosphoramidate;
3'-Deoxy-3'-fluoro-4'-vinyluridine-5'-(O-1-naphthyl-N—(S)-1-(benzyloxycarbonyl)ethyl phosphoramidate;
3'-Deoxy-3'-fluoro-4'-vinyluridine-5'-{N,N'-bis[(S)-1-(isopropoxycarbonyl)ethyl]phosphorodiamidate};
3'-Deoxy-3'-fluoro-4'-vinyluridine-5'-{N,N'-bis[(S)-1-(2,2-dimethylpropoxycarbonyl)ethyl]phosphorodiamidate};
3'-Deoxy-3'-fluoro-4'-vinyluridine-5'-{N,N'-bis[(S)-1-(cyclopentoxycarbonyl)ethyl]phosphorodiamidate};
3'-Deoxy-3'-fluoro-4'-vinylcytidine-5'-(O-1-naphthyl-N—(S)-1-(isopropoxycarbonyl)ethyl phosphoramidate;
3'-Deoxy-3'-fluoro-4'-vinylcytidine-5'-(O-1-naphthyl-N—(S)-1-(2,2-dimethylpropoxycarbonyl)ethyl phosphoramidate;
3'-Deoxy-3'-fluoro-4'-vinylcytidine-5'-(O-1-naphthyl-N—(S)-1-(benzyloxycarbonyl)ethyl phosphoramidate;
3'-Deoxy-3'-fluoro-4'-vinylcytidine-5'-{N,N'-bis[(S)-1-(propoxycarbonyl)ethyl]phosphorodiamidate};
3'-Deoxy-3'-fluoro-4'-vinylcytidine-5'-{N,N'-bis[(S)-1-(2,2-dimethylpropoxycarbonyl)ethyl]phosphorodiamidate};
3'-Deoxy-3'-fluoro-4'-vinylcytidine-5'-{N,N'-bis[(S)-1-(hexoxycarbonyl)ethyl]phosphorodiamidate}; and
3'-Deoxy-3'-fluoro-4'-vinylcytidine-5'-{N,N'-bis[(S)-1-(cyclopentoxycarbonyl)ethyl]phosphorodiamidate}.

13. A method for treating an RSV infection comprising administering to a patient in need thereof a therapeutically effective amount of the compound of claim 1.

14. A composition comprising the compound of claim 1.

15. A composition comprising the compound of claim 12.

\* \* \* \* \*